United States Patent
Benard et al.

(10) Patent No.: US 10,150,804 B2
(45) Date of Patent: Dec. 11, 2018

(54) COMPOSITIONS AND METHODS FOR IMAGING CANCER

(71) Applicants: BRITISH COLUMBIA CANCER AGENCY BRANCH, Vancouver (CA); THE UNIVERSITY OF BRITISH COLUMBIA, Vancouver (CA)

(72) Inventors: Francois Benard, Vancouver (CA); Kuo-Shyan Lin, Surrey (CA); David Perrin, Vancouver (CA); Zhibo Liu, Vancouver (CA); Maral Pourghiasian, Vancouver (CA)

(73) Assignees: BRITISH COLUMBIA CANCER AGENCY BRANCH, Vancouver, British Columbia; THE UNIVERSITY OF BRITISH COLUMBIA UNIVERSITY-INDUSTRY LIAISON OFFICE, Vancouver, British Columbia ( * ) Notice: Subject to any disclaimer, the term of this patent is extended or adjusted under 35 U.S.C. 154(b) by 86 days.

(21) Appl. No.: 15/109,551

(22) PCT Filed: Jan. 2, 2015

(86) PCT No.: PCT/CA2015/000002
§ 371 (c)(1),
(2) Date: Jul. 1, 2016

(87) PCT Pub. No.: WO2015/100498
PCT Pub. Date: Jul. 9, 2015

(65) Prior Publication Data
US 2016/0333068 A1 Nov. 17, 2016

Related U.S. Application Data

(60) Provisional application No. 61/923,233, filed on Jan. 3, 2014.

(51) Int. Cl.
*A61K 51/00* (2006.01)
*A61M 36/14* (2006.01)
*C07K 14/655* (2006.01)
*A61K 51/08* (2006.01)

(52) U.S. Cl.
CPC .......... *C07K 14/655* (2013.01); *A61K 51/083* (2013.01)

(58) Field of Classification Search
CPC ..... A61K 51/00; A61K 51/083; C07K 14/655
USPC ........ 424/1.11, 1.65, 1.69, 9.1, 9.2, 9.3, 9.4, 424/9.5, 9.6, 1.81, 1.85, 1.89; 514/1, 1.1, 514/11.1, 19.2, 19.3, 19.4, 19.5, 19.6, 514/21.1, 21.2, 21.3, 21.4, 21.5, 21.6, 514/21.7, 21.8, 21.9, 64; 530/300, 311, 530/317, 324, 325, 326, 327, 328, 329, 530/330, 331, 333, 334, 335
See application file for complete search history.

(56) References Cited

U.S. PATENT DOCUMENTS

| 5,650,134 A | 7/1997 | Albert et al. |
|---|---|---|
| 8,114,381 B2 | 2/2012 | Perrin et al. |
| 8,153,101 B2 | 4/2012 | McBride et al. |
| 8,574,546 B2 * | 11/2013 | Perrin .............. A61K 51/04 424/1.65 |
| 8,691,761 B2 | 4/2014 | Rivier et al. |
| 2014/0147381 A1 | 5/2014 | Espenan |

FOREIGN PATENT DOCUMENTS

| WO | WO 2005/077967 | 8/2005 |
|---|---|---|
| WO | WO 2009/012596 | 1/2009 |
| WO | WO 2012/094334 | 7/2012 |
| WO | WO 2012/118909 | 9/2012 |
| WO | WO 2014/134716 | 9/2014 |

OTHER PUBLICATIONS

Pourghiasian et al, Bioorganic & Medicinal Chemistry, vol. 23, No. 7, pp. 1500-1506. (Year: 2015).*
Liu et al, Molecular Pharmaceutics, vol. 12, No. 3, pp. 974-982. (Year: 2015).*
Liu et al, Journal of Nuclear Medicine, vol. 55, No. 9, pp. 1499-1505. (Year: 2014).*
Extended Search Report for European Patent Application No. 15733077.0, dated Jun. 19, 2017, 6 pages.
Antunes et al. "Influence of Different Spacers on the Biological Profile of a DOTA-Somatostatin Analogue," Bioconjugate Chemistry, 2007, vol. 18, pp. 84-92.
Banerjee et al. "Clinical applications of Gallium-68," Applied Radiation and Isotopes, 2013, vol. 76, pp. 2-13.
Breeman et al. "Somatostatin receptor-mediated imaging and therapy: basic science, current knowledge, limitations and future perspectives," European Journal of Nuclear Medicine, Sep. 2001, vol. 28, No. 9, pp. 1421-1429.
Buchmann et al. "Comparison of 68Ga-DOTATOC PET and 111In-DTPAOC (Octreoscan) SPECT in patients with neuroendocrine tumours," Eur J Nucl Med Mol Imaging., 2007, vol. 34, pp. 1617-1626.
Cai et al. "RGD-based PET tracers for imaging receptor integrin αvβ3 expression," Journal of Labelled Compounds and Radiopharmaceuticals, 2013, vol. 56, pp. 264-279.
Chin et al. "First Experience with Clinical-Grade [18F]FPP(RGD)2: An Automated Multi-step Radiosynthesis for Clinical PET Studies," Mol Imaging Biol., 2012, vol. 14 pp. 88-95.
Eberl et al. "High beam current operation of a PETtraceTM cyclotron for 18F production," Applied Radiation and Isotopes, 2012, vol. 70, pp. 922-930.

(Continued)

*Primary Examiner* — D. L. Jones
(74) *Attorney, Agent, or Firm* — Sheridan Ross P.C.

(57) ABSTRACT

Somatostatin derivative compounds of general formula (I) that may be readily labelled with the isotope fluorine-18 and that have affinity and selectivity for cellular somatostatin receptors are provided. The labelled compounds are useful clinically as radioactive tracers in various in vivo imaging applications (for example, using positron emission tomography (PET) and related techniques) to detect somatostatin-expressing cells and tissues, including tumors, or as therapeutic agents.

19 Claims, 11 Drawing Sheets
Specification includes a Sequence Listing.

(56) References Cited

OTHER PUBLICATIONS

Fani et al. "Unexpected Sensitivity of sst2 Antagonists to N-Terminal Radiometal Modifications," The Journal of Nuclear Medicine, Sep. 2012, vol. 53, No. 9, pp. 1481-1489.
Gabriel et al. "An Intrapatient Comparison of 99mTc-EDDA/HYNIC-TOC with 111In-DTPA-Octreotide for Diagnosis of Somatostatin Receptor-Expressing Tumors," The Journal of Nuclear Medicine, May 2003, vol. 44, No. 5, pp. 708-716.
Gabriel et al. "68Ga-DOTA-Tyr3-Octreotide PET in Neuroendocrine Tumors: Comparison with Somatostatin Receptor Scintigraphy and CT," The Journal of Nuclear Medicine, Apr. 2007, vol. 48, No. 4, pp. 508-518.
Ginj et al. "Design, Synthesis, and Biological Evaluation of Somatostatin-Based Radiopeptides," Chemistry & Biology, Oct. 2006, vol. 13, pp. 1081-1090.
Guo et al. "Preparation and Biological Evaluation of 64Cu Labeled Tyr3-Octreotate using a Phosphonic Acid-Based Cross-Bridged Macrocyclic Chelator," Bioconjugate Chemistry, 2012, vol. 23, pp. 1470-1477.
Henze et al. "PET Imaging of Somatostatin Receptors Using [68GA]DOTA-D-Phe1-Tyr3-Octreotide: Firest Results in Patients with Meningiomas," The Journal of Nuclear Medicine, Jul. 2001, vol. 42, No. 7, pp. 1053-1056.
Kayani "A Comparison of 68Ga-DOTATATE and 18F-FDG PET/CT in Pulmonary Neuroendocrine Tumors," The Journal of Nuclear Medicine, Dec. 2009, vol. 50, No. 12, pp. 1927-1932.
Kemerink et al. "Effect of the positron range of 18F, 68Ga and 124I on PET/CT in lung-equivalent materials," Eur J Nucl Med Mol Imaging, 2011, vol. 38, pp. 940-948.
Krausz et al. "SPECT/CT hybrid imaging with 111In-pentetreotide in assessment of neuroendocrine tumours," Clinical Endocrinology, 2003, vol. 59, pp. 565-573.
Kwekkeboom et al. "Peptide Receptor Radionuclide Therapy in Patients With Gastroenteropancreatic Neuroendocrine Tumors," Seminars in Nuclear Medicine, Mar. 2010, vol. 40, No. 2, pp. 78-88.
Kwekkeboom et al. "Somatostatin receptor-based imaging and therapy of gastroenteropancreatic neuroendocrine tumors," Endocr Relat Cancer., 2010, vol. 17, pp. R53-R73.
Laforest et al. "Image quality with non-standard nuclides in PET," QJ Nucl Med Mol Imaging, 2008, vol. 52, pp. 151-158.
Laverman et al. "A Novel Facile Method of Labeling Octreotide with 18F-Fluorine." Journal of Nuclear Medicine, Mar. 2010, vol. 51, No. 3, pp. 454-461.
Laverman et al. "Optimized labeling of NOTA-conjugated octreotide with F-18." Tumor Biol., 2012, vol. 33, pp. 427-434.
Leyton et al. "Targeting Somatostatin Receptors: Preclinical Evaluation of Novel 18F-Fluoroethyltriazole-Tyr3-Octreotate Analogs for PET." The Journal of Nuclear Medicine, Sep. 2011, vol. 52, No. 9, pp. 1441-1448.
Li et al. "One-step and one-pot-two-step radiosynthesis of cyclo-RGD-18F-aryltrifluoroboronate conjugates for functional imaging." Am. J. Nucl. Med. Mol. Imaging, 2013, vol. 3, No. 1, pp. 44-56.
Liu et al. "Preclinical Evaluation of a High-Affinity 18F-Trifluoroborate Octreotate Derivative for Somatostatin Receptor Imaging." The Journal of Nuclear Medicine, Sep. 2014, vol. 55, No. 9, pp. 1499-1505.
Liu et al. "An Organotrifluoroborate for Broadly Applicable One-Step 18F-Labeling," Angew Chem Int Ed., 2014, vol. 53, pp. 11876-11880.
Liu et al. "Stoichiometric Leverage: Rapid 18F-Aryltrifluoroborate Radiosynthesis at High Specific Activity for Click Conjugation," Angew. Chem. Int. Ed., 2013, vol. 52, pp. 2303-2307.
Liu et al. "Rapid, one-step, high yielding 18F-labeling of an aryltrifluoroborate bioconjugate by isotope exchange at very high specific activity," Journal of Labelled Compounds and Radiopharmaceuticals, 2012, vol. 55, pp. 491-496.
Liu et al. "Kit-like 18F-labeling of RGD-19F-Arytrifluroborate in high yeald and at extraordinarily high specific activity with preliminary in vivo tumor imaging," Nuclear Medicine and Biology, vol. 40, 2013, pp. 841-849.
Liu et al. "Preclinical Evaluation of a Novel 18F-Labelled Somatostatin Receptor-Binding Peptide—Abstract Proof," ScholarOne, Inc., 2014, Control ID: 1931699, 4 pages.
Liu et al. "Facile synthesis and biological evaluation of an 18F-labeled 4-(2-aminoethyl) benzenesulfonamide (AEBS) trimer for imaging carbonic anhydrase IX expression with positron emission tomography," World Molecular Imaging Congress, Sep. 19, 2013, Presentation No. LBAP 029, 2 pages.
Liu et al. ""Kit-like" radiosynthesis and biological evaluation of an F-labeled 4-(2-Aminoethyl)-benzenesulfonamide (AEBS) trimer for imaging carbonic anhydrase IX expression with positron emission tomography," World Molecular Imaging Congress, Sep. 19, 2013—poster, 1 page.
Liu et al. "Preclinical evaluation of a high affinity 18F-trifluoroborate octreotate derivative for somatostatin receptor imaging—poster," UBC, 2014, 1 page.
Liu et al. "Preclinical evaluation of a novel F-labelled somatostatin receptor-binding peptide," The Journal of Nuclear Medicine, 2014, vol. 55 (Supplement 1):1089, 1 page.
Matteson et al. "Iodomethaneboronic Esters and Aminomethaneboronic Esters," Journal of Organometallic Chemistry, 1979, vol. 170, pp. 259-264.
Means et al. "Chemical Modifications of Proteins: History and Applications," Bioconjugate Chemistry, 1990, vol. 1, No. 1, pp. 2-12.
Poeppel et al. "68Ga-DOTATOC Versus 68Ga-DOTATATE PET/CT in Functional Imaging of Neuroendocrine Tumors," The Journal of Nuclear Medicine, Dec. 2011, vol. 52, No. 12, pp. 1864-1870.
Poethko et al. "Two-Step Methodology for High-Yield Routine Radiohalogenation of Peptides: 18F-Labeled RGD and Octreotide Analogs," The Journal of Nuclear Medicine, May 2004, vol. 45, No. 5, pp. 892-902.
Reubi et al. "Affinity profiles for human somatostatin receptor subtypes SST1-SST5 of somatostatin radiotracers selected for scintigraphic and radiotherapeutic use," European Journal of Nuclear Medicine, Mar. 2000, vol. 27, No. 3, pp. 273-282.
Sprague et al. "Preparation and Biological Evaluation of Copper-64-Labeled Tyr3-Octreotate Using a Cross-Bridged Macrocyclic Chelator," Clinical Cancer Research, Dec. 2004, vol. 10, pp. 8674-8682.
Storch et al. "Evaluation of [99mTc/EDDA/HYNIC0]Octreotide Derivatives Compared with [111In-DOTA0,Tyr3, Thr8]Octreotide and [111In-DTPA0]Octreotide: Does Tumor or Pancreas Uptake Correlate with the Rate of Internalization?" The Journal of Nuclear Medicine, Sep. 2005, vol. 46, No. 9, pp. 1561-1569.
Vallabhajosula et al. "Preclinical Evaluation of Technetium-99m-Labeled Somatostatin Receptor-Binding Peptides," The Journal of Nuclear Medicine, Jun. 1996, vol. 37, No. 6, pp. 1016-1022.
Virgolini et al. "Somatostatin Receptor Subtype Specificity and in Vivo Binding of a Novel Tumor Tracer, 99mTc-P8291," Cancer Research, May 1998, vol. 58, pp. 1850-1859.
Wangler et al. "One-Step 18F-Labeling of Carbohydrate-Conjugated Octreotate-Derivatives Containing a Silicon-Fluoride-Acceptor (SiFA): In Vitro and in Vivo Evaluation as Tumor Imaging Agents for Positron Emission Tomography (PET)," Bioconjug Chem., 2010, vol. 21, No. 12, pp. 2289-2296.
Wester et al. "PET imaging of somatostatin receptors: design, synthesis and preclinical evaluation of a novel 18F-labelled, carbohydrated analogue of octreotide," European Journal of Nuclear Medicine and Molecular Imaging, Jan. 2003, vol. 30, No. 1, pp. 117-122.
Zhan et al. "Hydration of the Fluoride Anion: Structures and Absolute Hydration Free Energy from First-Principles Electronic Structure Calculations," J Phys Chem A., 2004, vol. 108, pp. 2020-2029.
International Search Report and Written Opinion for International (PCT) Patent Application No. PCT/CA2015/000002, dated May 4, 2015, 10 pages.

* cited by examiner

2

3

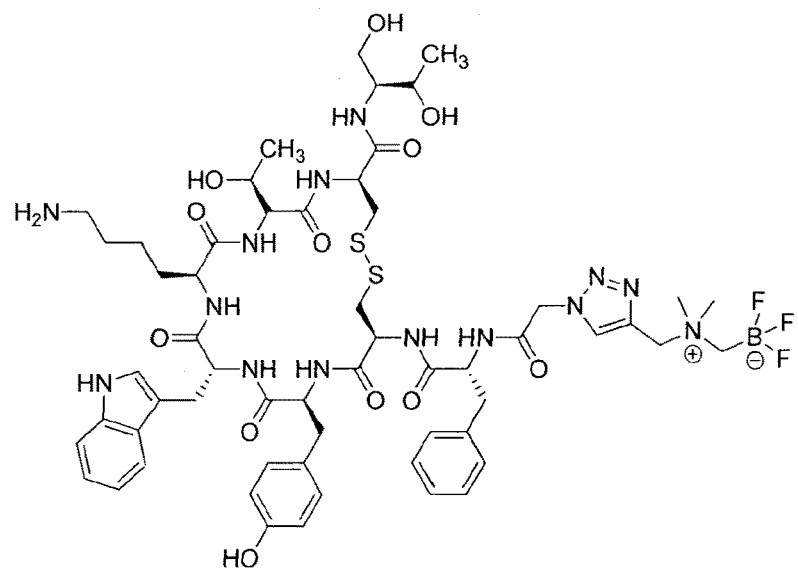
6
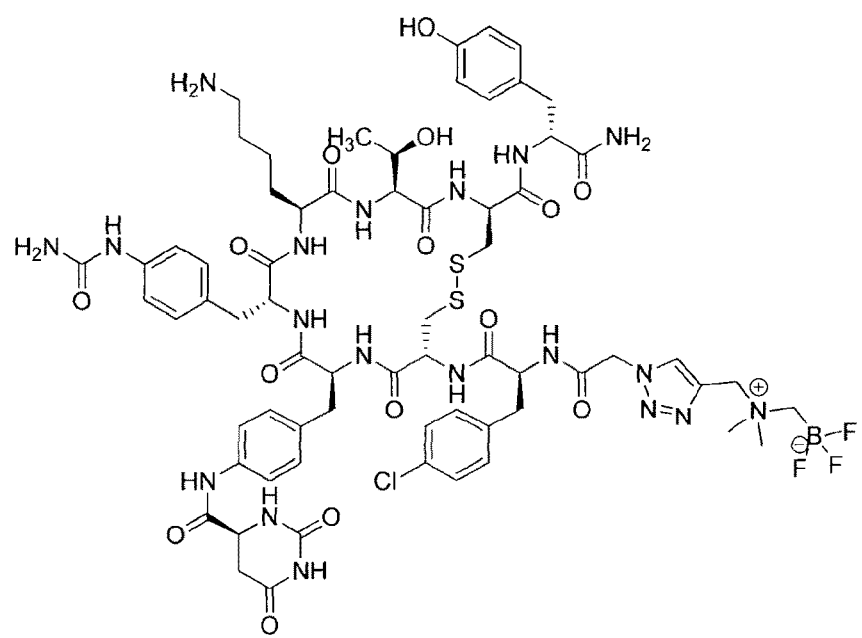
7
FIG. 8 (con.)

COMPOSITIONS AND METHODS FOR IMAGING CANCER

CROSS REFERENCE TO RELATED APPLICATIONS

This application is a national stage application under 35 U.S.C. 371 and claims the benefit of PCT Application No. PCT/CA2015/000002 having an international filing date of 2 Jan. 2015, which designated the United States, which PCT application claimed the benefit of U.S. Provisional Application No. 61/923,233, filed 3 Jan. 2014, the disclosures of each of which are incorporated herein by reference.

FIELD OF THE INVENTION

The present invention relates to the field of radioimaging and, in particular, to radiolabelled compounds, methods of preparing the compounds and their use in imaging cancer.

BACKGROUND OF THE INVENTION

The somatostatin receptor subtype 2 (sstr2) is overexpressed in many neuroendocrine tumours. Hence over the past 30 years, there has been considerable interest in developing high-affinity somatostatin-derived ligands that bind sstr2, notably for radionuclide therapy (Kwekkeboom D J, et al., Semin Nucl Med. 2010, 40:78-88). To diagnose and monitor patients with sstr2-positive tumours, radiotracers based on the somatostatin family of peptides, notably octreotate and octreotide, have been labelled with various radioisotopes for non-invasive imaging (Breeman W A P, et al., Eur J Nucl Med., 2001, 28:1421-1429; Ginj M, et al., Chem Biol., 2006, 13:1081-1090; Antunes P, et al., Bioconjug Chem., 2007, 18:84-92; Kwekkeboom D J, et al., Endocr Relat Cancer., 2010, 17:R53-R73). $^{111}$In-diethylenetriaminepentaacetic acid-pentetreotide (Octreoscan™; Mallinckrodt) is the current clinical standard for imaging neuroendocrine tumours (Krausz Y, et al., Clin Endocrinol (Oxf)., 2003, 59:565-573; Buchmann I, et al., Eur J Nucl Med Mol Imaging, 2007, 34:1617-1626; Storch D, et al., J Nucl Med., 2005, 46:1561-1569). $^{99m}$Tc derivatives such as $^{99m}$Tc-depreotide (Virgolini I, et al., Cancer Res., 1998, 58:1850-1859) and $^{99m}$Tc-hydrazinonicotinyl-Tyr3-octreotide have also been used (Gabriel M, et al., J Nucl Med., 2003, 44:708-716) but are not commercialized in North America.

For PET imaging, $^{68}$Ga, $^{64}$Cu, and $^{18}$F along with various radioprosthetics have been conjugated to various octreotide derivatives (Sprague J E, et al., Clin Cancer Res., 2004, 10:8674-8682; Gabriel M, et al., J Nucl Med., 2007, 48:508-518; Guo Y, et al., Bioconjug Chem., 2012, 23:1470-1477; Wester H J, et al., Eur J Nucl Med Mol Imaging, 2003, 30:117-122; Poethko T, et al., J Nucl Med., 2004, 45:892-902; Leyton J, et al., J Nucl Med., 2011, 52:1441-1448, and International Patent Application Publication No. WO2012/118909). Of these, certain $^{68}$Ga ligands such as $^{68}$Ga-DOTATOC, $^{68}$Ga-DOTATATE, and $^{68}$Ga-DOTANOC have shown promise for neuroendocrine tumour imaging (Henze M, et al., J Nucl Med., 2001, 42:1053-1056; Kayani I, et al., J Nucl Med., 2009, 50:1927-1932; Poeppel T D, et al., J Nucl Med., 2011, 52:1864-1870) and are used in clinical trials as well as under the local practice of pharmacy, particularly in Europe. Nevertheless, $^{68}$Ga-PET imaging is not widely available because of the limited daily availability of $^{68}$Ga (~50 mCi) and the lack of FDA-approved $^{68}$Ge/$^{68}$Ga generators (Banerjee S R, Pomper M G., Appl Radiat Isot., 2013, 76:2-13).

$^{18}$F-fluoride presents several attractive properties for imaging (Laforest R, Liu X., Q J Nucl Med Mol Imaging, 2008, 52:151-158; Kemerink G J, et al., Eur J Nucl Med Mol Imaging, 2011, 38:940-948) and is produced on a daily basis in large quantities in hundreds of cyclotrons in hospitals and radiopharmacies worldwide. Yet the challenges of labelling peptides with $^{18}$F-fluoride are significant: the low chemical reactivity of $^{18}$F-fluoride in water (Zhan C-G, Dixon D A., J Phys Chem A., 2004, 108:2020-2029) and short half-life (109.8 min) challenge $^{18}$F labeling of peptides that are generally soluble only in water or aqueous cosolvents. Hence, fluoride must be dried and reacted in dry solvents at high temperature to radiolabel a radioprosthetic that is then conjugated to the peptide in at least one additional step. Although such multistep $^{18}$F-labeling reactions are commonplace (Chin F T, et al., Mol Imaging Biol., 2012, 14:88-95), the relatively short half-life of $^{18}$F-fluoride often impedes the clinical application of multistep reactions, particularly in terms of ensuring specific activity greater than 37 GBq/μmol (>1 Ci/μmol) (Cai H, Conti P S., J Labelled Comp Radiopharm., 2013, 56:264-279). Given these challenges, an sstr2 ligand that is easily labelled with $^{18}$F-fluoride in high yield and at high specific activity would facilitate sstr2 imaging by PET. Toward these ends, new $^{18}$F-octreotate derivatives, such as $^{18}$F-SiFA and Al-$^{18}$F-NOTA, have been labelled in one step and imaged with relative success (Wangler C, et al., Bioconjug Chem., 2010, 21:2289-2296; Laverman P, et al., Tumour Biol., 2012, 33:427-434; Laverman P, et al., J Nucl Med., 2010, 51:454-461).

Similarly, aryltrifluoroborate prosthetics, when conjugated to various peptides, allow one-step aqueous radiofluorination in high yield and very high specific activity (Liu Z, et al., J Labelled Comp Radiopharm., 2012, 14:491-497; Liu Z, et al., Nucl Med Biol., 2013, 40:841-849; Liu Z, et al., Angew Chem Int Ed., 2013, 52:2305-2307, and International Patent Application Publication No. WO2009/012596).

Another methodology for incorporating $^{18}$F into imaging agents that makes use of boron as an acceptor capable of binding several $^{18}$F atoms, thus increasing the density of positron emitters in the resulting imaging agent, is described in International Patent Application Publication No. WO2005/0077967 and U.S. Pat. No. 8,114,381.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

The present invention relates generally to compositions and methods for imaging cancer. One aspect of the invention relates to a fluorinated somatostatin derivative having general formula (I):

$$B^-F_3-(CH_2)_n-N^+R^1R^2-L-X \qquad (I)$$

wherein:
R$^1$ and R$^2$ are each independently H, C$_1$-C$_6$ alkyl, C$_3$-C$_6$ cycloalkyl, or C$_3$-C$_6$ aryl;

L is a linking group;

X is a somatostatin analogue conjugated via an N-terminal amino group to L, and n is 1 or 2, and wherein the somatostatin analogue is capable of binding to a somatostatin receptor.

Another aspect of the invention relates to a fluorinated somatostatin derivative selected from: $AMBF_3$-TATE (compound 2), $AMBF_3$-JR11 (compound 7), $AMBF_3$-LM3 (compound 3) and $AMBF_3$-TOC (compound 6).

The fluorinated somatostatin derivative according to any one of claims 1 to 19, wherein each F is $^{19}F$.

fluorinated somatostatin derivative according to any one of claims 1 to 19, wherein at least one F is $^{18}F$.

The fluorinated somatostatin derivative according to claim 21, wherein each F is $^{18}F$.

Another aspect of the invention relates to a method of preparing a $^{18}F$-labelled somatostatin derivative comprising submitting a fluorinated somatostatin derivative as described above in which each F is $^{19}F$ to an isotope exchange reaction using $^{18}F$-fluoride.

Another aspect of the invention relates to an $^{18}F$-labelled somatostatin derivative prepared by a method as described above.

Another aspect of the invention relates to a use of a fluorinated somatostatin derivative as described above in which at least one F is $^{18}F$ as a radiotracer.

Another aspect of the invention relates to a use of a fluorinated somatostatin derivative as described above in which at least one F is $^{18}F$ as a positron emission tomography (PET) imaging agent.

Another aspect of the invention relates to a use of a fluorinated somatostatin derivative as described above in which each F is $^{19}F$ as a therapeutic agent.

Another aspect of the invention relates to a kit for the preparation of a $^{18}F$-labelled imaging agent comprising a fluorinated somatostatin derivative as described above in which each F is $^{19}F$ and optionally instructions for use.

BRIEF DESCRIPTION OF THE DRAWINGS

These and other features of the invention will become more apparent in the following detailed description in which reference is made to the appended drawings.

DETAILED DESCRIPTION OF THE INVENTION

Figure 1:
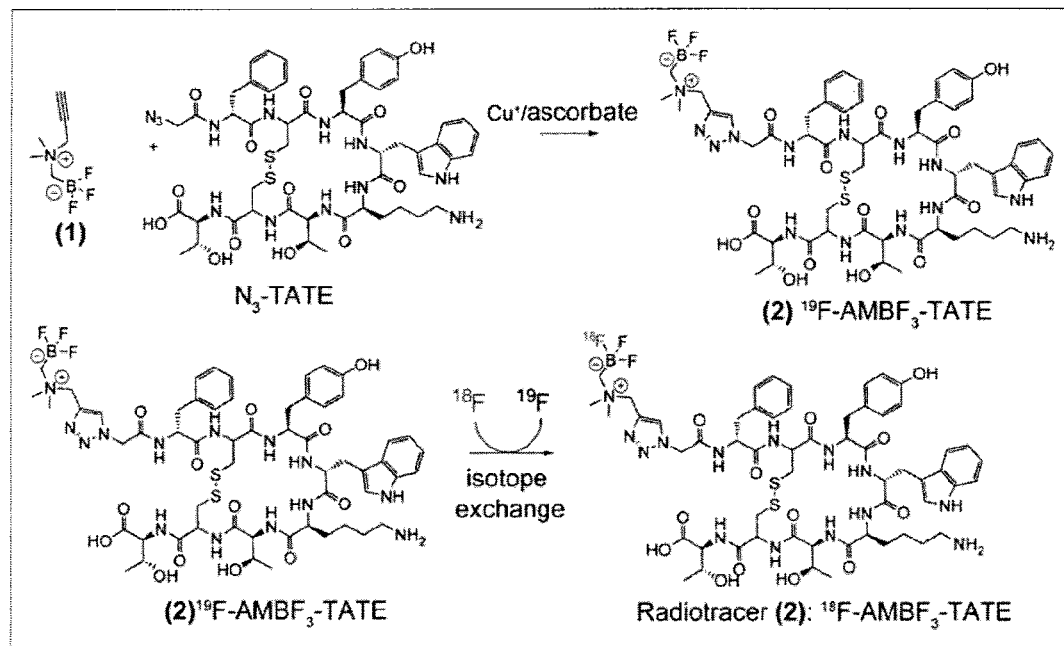
FIG. 1 depicts the synthesis of a radiotracer, $^{18}F$-$AMBF_3$-TATE in one embodiment of the invention: $N_3$-TATE is condensed with N-propargyl-N,N-dimethyl-ammoniomethyltrifluoroborate (1) to provide precursor $AMBF_3$-TATE (2). Precursor 2 is labelled by isotope exchange to provide isotopolog $^{18}F$-2 at high specific activity for tracer studies.

In broad terms this invention relates to somatostatin derivative compounds that may be readily labelled with the isotope fluorine-18 and that have affinity and selectivity for cellular somatostatin receptors. The labelled compounds are useful clinically as radioactive tracers in various in vivo imaging applications (for example, using positron emission tomography (PET) and related techniques) to detect somatostatin-expressing cells and tissues, including tumours.

The somatostatin derivatives may be based on a variety of somatostatin analogues provided that the selected somatostatin analogue is capable of selectively binding to a somatostatin receptor. In certain embodiments, the somatostatin derivatives are octreotide derivatives. In some embodiments, the invention relates to easily radiolabelled, high-affinity octreotide derivatives for imaging of somatostatin receptors in cancer (for example, neuroendocrine tumours) utilizing the commonly available $^{18}$F isotope that is used in PET imaging and used on a daily basis in most medical cyclotrons.

The unlabelled somatostatin derivatives can be readily labelled by isotope exchange in a single vessel reaction, and free fluoride conveniently removed by simple solid phase extraction (SPE), with no requirement for HPLC purification. Certain embodiments of the invention thus relate to the provision of unlabelled somatostatin derivatives in kit format for labelling just prior to use.

As shown herein, an exemplary labelled somatostatin derivative compound, $^{18}$F-AMBF$_3$-TATE, exhibited higher than expected affinity for somatostatin receptors, together with low liver uptake, resulting in a higher than expected tumour-to-liver ratio. In addition, in certain embodiments of the invention, the trifluoroboronate moiety included in the somatostatin derivative compounds of the present disclosure provides for a simplified labelling due to one or more of: requiring only submilligram quantities of unlabelled precursor compound for labelling; obviating the need for azeotropic fluoride drying through the use of no-carrier-added $^{18}$F-fluoride directly for an aqueous labelling reaction; allowing for rapid (for example, less than 30 min) labelling; providing labelled compounds with high specific activity, and/or removing the requirement for HPLC purification as the unlabelled precursor is chemically identical to the product.

In certain embodiments, the simplified labelling procedure can allow for yields that provide multiple human doses in a single run. In some embodiments, the process is readily amenable to automation and/or microfluidic flow technologies.

Definitions

Unless defined otherwise, all technical and scientific terms used herein have the same meaning as commonly understood by one of ordinary skill in the art to which this invention belongs.

The term "C$_1$-C$_6$ alkyl," as used herein, refers to a substituted or unsubstituted straight chain or branched hydrocarbon of one to six carbon atoms. This term is exemplified by such groups as methyl, ethyl, n-propyl, i-propyl, n-butyl, t-butyl, i-butyl, isopentyl, n-pentyl, hexyl, and the like.

The term "C$_3$-C$_6$ cycloalkyl" refers to a substituted or unsubstituted cyclic alkyl group containing 3 to 6 carbon atoms.

The term "C$_3$-C$_6$ aryl" refers to a substituted or unsubstituted aromatic cycloalkyl group having 3 to 6 carbon atoms.

The term "substituted" when used with one of the foregoing terms indicates that the named group is substituted at one or more positions with a group such as hydroxyl, thiol, alkylthiol, halogen, alkoxy, amino, amido, carboxyl, acyl, carboxyl, nitro or cyano.

As used herein, the term "about" refers to an approximately +/−10% variation from a given value. It is to be understood that such a variation is always included in any given value provided herein, whether or not it is specifically referred to.

The use of the word "a" or "an" when used herein in conjunction with the term "comprising" may mean "one," but it is also consistent with the meaning of "one or more," "at least one" and "one or more than one."

As used herein, the terms "comprising," "having," "including" and "containing," and grammatical variations thereof, are inclusive or open-ended and do not exclude additional, unrecited elements and/or method steps. The term "consisting essentially of" when used herein in connection with a composition, use or method, denotes that additional elements and/or method steps may be present, but that these additions do not materially affect the manner in which the recited composition, method or use functions. The term "consisting of" when used herein in connection with a composition, use or method, excludes the presence of additional elements and/or method steps. A composition, use or method described herein as comprising certain elements and/or steps may also, in certain embodiments consist essentially of those elements and/or steps, and in other embodiments consist of those elements and/or steps, whether or not these embodiments are specifically referred to.

It is contemplated that any embodiment discussed herein can be implemented with respect to any of the disclosed methods, uses, kits or compositions of the invention, and vice versa.

Somatostatin Derivatives

The somatostatin derivatives according to the present disclosure are fluorinated compounds of general formula (I):

$$B^-F_3\text{---}(CH_2)_n\text{---}N^+R^1R^2\text{-L-X} \qquad (I)$$

wherein:
R$^1$ and R$^2$ are each independently H, C$_1$-C$_6$ alkyl, C$_3$-C$_6$ cycloalkyl, or C$_3$-C$_6$ aryl;
L is a linking group;
X is a somatostatin analogue conjugated via an N-terminal amino group to L, and
n is 1 or 2.

Generally, the somatostatin analogue is a peptidic compound that is capable of binding to a somatostatin receptor. In certain embodiments, the somatostatin analogue is capable of binding to the somatostatin receptor subtype 2 (sstr2). In some embodiments, the somatostatin analogue is capable of selectively binding to the somatostatin receptor subtype 2 (sstr2).

In certain embodiments, in compounds of general formula (I), R$^1$ and R$^2$ are each independently C$_1$-C$_6$ alkyl. In certain embodiments, in compounds of general formula (I), R$^1$ and R$^2$ are each independently C$_1$-C$_4$ alkyl.

In certain embodiments, in compounds of general formula (I), n is 1.

One skilled in the art will appreciate that compounds of general formula (I) may be readily prepared by conjugation of an appropriately derivatized trifluoroboronate moiety to either the naturally-occurring amine group at the N-terminus of the somatostatin analogue X, or to an appropriately N-terminally derivatized somatostatin analogue. Accordingly, the nature of the linking group L in the compounds of general formula (I) will be dependent on the method by which the compound was prepared.

A variety of synthetic chemical groups that will form chemical bonds with primary amines are known in the art. Examples include, but are not limited to, isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl ester, most of which conjugate to amines by either acylation or alkylation. In accordance with certain embodiments, therefore, the linking group L may comprise formula (VII):

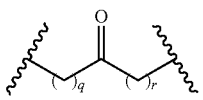

(VII)

wherein q and r are each independently 0 to 15.
or formula (VIII):

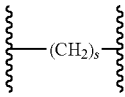

(VIII)

wherein s is 1 to 15.

In certain embodiments, L in the compounds of general formula (I) comprises formula (VII) in which each of q and r are independently 0 to 10. In some embodiments, L in the compounds of general formula (I) comprises formula (VII) in which each of q and r are independently 0 to 6. In some embodiments, L in the compounds of general formula (I) comprises formula (VII) in which each of q and r are independently 0 to 4.

In certain embodiments, L in the compounds of general formula (I) comprises formula (VIII) in which s is 1 to 10. In some embodiments, L in the compounds of general formula (I) comprises formula (VIII) in which s is 1 to 6. In some embodiments, L in the compounds of general formula (I) comprises formula (VIII) in which s is 1 to 4.

Alternative approaches to conjugation of proteins and peptides to other groups are known in the art. For example, chemical modification of proteins is described in G. E. Means and R. E. Feeney, Bioconjugate Chemistry, 1990, 1:2-12.

In certain embodiments, the somatostatin analogue is conjugated to the trifluoroboronate moiety via copper-catalyzed azide-alkyne cycloaddition ("click" chemistry). In accordance with some embodiments, therefore, the linking group L will comprise a 1,2,3-triazole moiety:

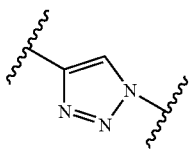 [SMILES: *c1cn(*)nn1]

In some embodiments, linking group L comprises formula (II):

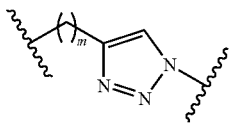

(II)

wherein: m is 1 to 15.

In certain embodiments, L in the compounds of general formula (I) comprises formula (II) in which m is 1 to 10. In some embodiments, L in the compounds of general formula (I) comprises formula (II) in which m is 1 to 6. In some embodiments, L in the compounds of general formula (I) comprises formula (II) in which m is 1 to 4. In some embodiments, L in the compounds of general formula (I) comprises formula (II) in which m is 1 or 2.

In some embodiments, L is a linking group of formula (III):

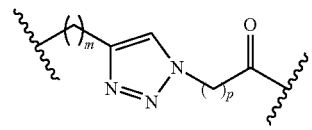

(III)

wherein: m is 1 to 15 and p is 1 to 8.

In certain embodiments, L in the compounds of general formula (I) comprises formula (III) in which m and p are each independently 1 to 8. In some embodiments, L in the compounds of general formula (I) comprises formula (III) in which m and p are each independently 1 to 6. In some embodiments, L in the compounds of general formula (I) comprises formula (III) in which m and p are each independently 1 to 4.

In certain embodiments, L is a linking group of formula (III) in which m is 1. In some embodiments, L is a linking group of formula (III) in which p is 1.

In some embodiments, L is:

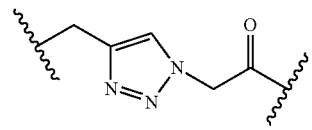

Various somatostatin analogues are known in the art and may be used to prepare the fluorinated somatostatin derivative of general formula (I). As noted above, the somatostatin analogues are generally peptidic compounds. By "peptidic compound" it is meant a compound that comprises a sequence of amino acids, which may be naturally-occurring amino acids, non-naturally occurring amino acids or a combination thereof. In some embodiments, the somatostatin analogue may comprise all or a part of a naturally-occurring somatostatin amino acid sequence. In some embodiments, the somatostatin analogue may comprise a part of a naturally-occurring somatostatin amino acid sequence and may further comprise one or more modified amino acids and/or additional amino acid sequences. The one or more modified amino acids may be modified in that the naturally-occurring amino acid is substituted with a different naturally-occurring amino acid, or it may be substituted with a non-naturally occurring amino acid.

Naturally-occurring human somatostatins include the art-known 14-amino acid and 28-amino acid forms of somatostatin (SEQ ID NOs: 1 and 2, respectively), the sequences of which are known and publicly available from various databases.

```
Somatostatin-14:
                                    [SEQ ID NO: 1]
AGCKNFFWKTFTSC
(disulfide bridge present between Cys 3 and
Cys 14)

Somatostatin-28:
                                    [SEQ ID NO: 2]
SANSNPAMAPRERKAGCKNFFWKTFTSC
(disulfide bridge present between Cys 17 and
Cys 28)
```

Various non-naturally occurring amino acids are known in the art. Examples include, but are not limited to, D-amino acids (i.e. an amino acid of an opposite chirality to the naturally occurring form), N-α-methyl amino acids, C-α-methyl amino acids, β-methyl amino acids and D- or L-β-amino acids. More specific examples include, but are not limited to, 2-aminobutyric acid (Abu), 4-aminobutyric acid (γ-Abu), 6-aminohexanoic acid (ε-Ahx or Ahx), α-aminoisobutyric acid (Aib), β-alanine (β-Ala), β-aspartic acid (β-Asp), β-cyclohexylalanine (Cha), α-cyclohexylglycine (Chg), citrulline (Cit), diaminobutyric acid (Dab), diaminopimelic acid (Dap), γ-glutamic acid (γ-Glu), pyroglutamic acid (pGlu), homocysteine (Hcy), homoserine (Hse), hydroxyproline (Hyp), N-ε-dinitrophenyl-lysine (Lys (Dnp)), N-ε-methyl-lysine (Lys(Me)), N,N-ε-dimethyl-lysine (Lys(Me$_2$)), N,N,N-ε-trimethyl-lysine (Lys(Me$_3$)), 3-mercaptopropionic acid (Mpa), L-1-napthylalanine (L-1-Nal), L-2-napthylalanine (L-2-Nal), norleucine (Nle), norvaline (Nva), norleucine (Nle), ornithine (Orn), 3-(2-pyridyl)-L-alanine (L-2-Pal), 3-(3-pyridyl)-L-alanine (L-2-Pal), 3-(4-pyridyl)-L-alanine (L-4-Pal), penacillamine (Pen), 4-chlorophenyl-L-alanine (L-4-Cl-Phe), 4-fluorophenyl-L-alanine (L-4-F-Phe), 4-iodophenyl-L-alanine (L-4-I-Phe), 4-nitrophenyl-L-alanine (L-4-NO$_2$-Phe), phenylglycine (Phg), sarcosine (Sar), D-2-methyl-tryptophan (D-2-Me-Trp), phosphor-serine (pSer), phosphor-threonine (pThr), phosphor-tyrosine (pTyr), 1-amino-3.6.9,-trioxa-undecanoic acid (mini-PEG), cysteic acid, cyclohexylalanine, t-butylglycine, t-butylalanine, 3-aminopropionic acid, 2,3-diaminopropionic acid (2,3-diaP), D-2-naphthylalanine (D-2-Nal), 1,2,3,4-tetrahydroisoquinoline-3-carboxylic acid (Tic), octahydroindole-2-carboxylic acid (Oic), α-cyclopentylglycine (Cpg), 2-indanylglycine (Ig1), D- or L-2-thienylalanine (Thi), D- or L-3-thienylalanine, D- or L-1-, 2-, 3- or 4-pyrenylalanine, D-(2-pyridinyl)-alanine, D-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylalanine, D- or L-p-methoxybiphenylalanine, methionine sulphoxide (MSO) and homoarginine (Har). Other examples include substituted β-alanine (β-Ala) comprising one or more substituents selected from arylsulphonyl (such as benzenesulphonyl or 2-naphthalene sulphonyl) and alkoxycarbonyl (such as t-butoxycarbonyl); phosphono- or sulphated (e.g. —SO$_3$H) non-carboxylate amino acids; D- or L-2-indole(alkyl)alanines, and D- or L-alkylalanines, wherein alkyl is substituted or unsubstituted methyl, ethyl, propyl, hexyl, butyl, pentyl, hexyl, octyl, isopropyl, iso-butyl, or iso-pentyl.

Examples of known somatostatin analogues that may be included in the compounds of general formula (I) in some embodiments include, but are not limited to, octreotide and octreotide derivatives. Examples of octreotide derivatives include, but are not limited to, octreotate, [Tyr$^3$]octreotate (TATE), JR-11, JR-10, LM3, [Tyr$^3$]octreotide (TOC) and [Nal$^3$]octreotide (NOC).

In certain embodiments, the somatostatin analogue comprised by the somatostatin derivative of general formula (I) is:
  Octreotide: d-Phe-c[Cys-Phe-d-Trp-Lys-Thr-Cys]-Thr-ol;
  Octreotate: d-Phe-c[Cys-Phe-d-Trp-Lys-Thr-Cys]-Thr,
  TATE: d-Phe-c[Cys-Tyr-d-Trp-Lys-Thr-Cys]-Thr;
  JR-11: Cpa-c[d-Cys-Aph(Hor)-d-Aph(Cbm)-Lys-Thr-Cys]-d-Tyr-NH$_2$;
  LM3: p-Cl-Phe-c[d-Cys-Tyr-d-Aph(Cbm)-Lys-Thr-Cys]-d-Tyr-NH$_2$;
  JR-10: p-NO$_2$-Phe-c[d-Cys-Tyr-d-Aph(Cbm)-Lys-Thr-Cys]-d-Tyr-NH$_2$;
  TOC: d-Phe-c[Cys-Tyr-d-Trp-Lys-Thr-Cys]-Thr-ol,
  or NOC: d-Phe-c[Cys-1-Nal-d-Trp-Lys-Thr-Cys]-Thr-ol,
  wherein "Cpa" refers to cyclopentylalanine; "Aph(Hor)" refers to 4-[2,6-dioxo-hexahydro-pyrimidine-4-carbonyl)-amino]-phenylalanine; "Aph(Cbm)" refers to 4-ureido-phenylalanine, and "Nal" refers to napthylalanine.

In certain embodiments, the somatostatin analogue comprised by the somatostatin derivative of general formula (I) is: TATE, LM3, JR-11 or TOC.

Combinations of any of the foregoing embodiments for compounds of general Formula (I) are also contemplated and each combination forms a separate embodiment for the purposes of the present disclosure.

In certain embodiments, the compounds of general formula (I) have general formula (Ia):

$$B^-F_3-CH_2-N^+R^1R^2-L-X \quad (Ia)$$

wherein: $R^1$, $R^2$, L and X are as defined in any one of embodiments set forth above for general formula (I).

In some embodiments, the somatostatin derivatives are compounds of general formula (Ia) in which $R^1$ and $R^2$ are each independently $C_1$-$C_6$ alkyl. In some embodiments, the somatostatin derivatives are compounds of general formula (Ia) in which $R^1$ and $R^2$ are each independently $C_1$-$C_4$ alkyl. In some embodiments, the somatostatin derivatives are compounds of general formula (Ia) in which $R^1$ and $R^2$ are each independently $C_1$ or $C_2$ alkyl.

In some embodiments, the somatostatin derivatives are compounds of general formula (Ia) in which $R^1$ and $R^2$ are each independently $C_1$-$C_6$ alkyl, and L is a linking group of formula (II) or (III).

In certain embodiments, the compounds of general formula (I) have general formula (IV):

$$B^-F_3-CH_2-N^+(Me)_2-L-X \quad (IV)$$

wherein:
L and X are as described in any one of the embodiments set forth above for general formula (I).

In some embodiments, the somatostatin derivatives are compounds of general formula (IV) in which L is a linking group of formula (II) or (III).

In some embodiments, the somatostatin derivatives are compounds of general formula (IV) in which X is octreotate, TATE, JR-11, JR-10, LM3, TOC or NOC.

In certain embodiments, compounds of general formula (I) have general formula (V):

(V)

[Structure showing BF$_3^-$ group connected via $(CH_2)_n$ to N$^+$(CH$_3$)$_2$ connected via $(CH_2)_m$ to a triazole ring connected via $(CH_2)_p$ to C(=O)-X]

wherein, m and p are each independently 1 to 8, and n and X are as described in any one of the embodiments set forth above for general formula (I).

In some embodiments, the somatostatin derivatives are compounds of general formula (V) in which m and p are each independently 1 to 4.

In some embodiments, the somatostatin derivatives are compounds of general formula (V) in which n is 1.

In some embodiments, the somatostatin derivatives are compounds of general formula (V) in which X is octreotate, TATE, JR-11, JR-10, LM3, TOC or NOC.

In certain embodiments, compounds of general formula (I) have general formula (VI):

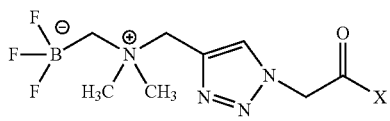

(VI)

wherein, X is as described in any one of the embodiments set forth above for general formula (I).

For ease of reference, a compound of general formula (VI) may also be referred to herein as AMBF$_3$-X. For example, a compound of general formula (VI) in which the somatostatin analogue X is octreotide may be referred to as AMBF$_3$-octreotide.

In certain embodiments, the fluorinated somatostatin derivative is selected from: AMBF$_3$-TATE (see FIG. 8; compound 2), AMBF$_3$-LM3 (see FIG. 8; compound 3), AMBF$_3$-NOC, AMBF$_3$-TOC (see FIG. 8; compound 6), AMBF$_3$-JR10 and AMBF$_3$-JR11 (see FIG. 8; compound 7).

The fluorinated somatostatin derivatives can be easily labelled with the isotope $^{18}$F (for example, by using isotope exchange as shown in FIG. 1 and described in more detail below) to provide the corresponding radioactive tracer compound.

It is to be understood that reference to compounds of general Formula (I) throughout the following disclosure, includes in various embodiments, compounds of general Formulae (IV), (V) and (VI) to the same extent as if embodiments reciting each of these formulae individually were specifically recited.

Methods of Preparation

Fluorinated Somatostatin Derivatives

The fluorinated somatostatin derivatives of general formula (I) can be readily prepared by standard peptide and synthetic chemistry techniques.

Somatostatin analogue X may be prepared, for example, by standard solid-phase synthesis methods and derivatized as necessary for conjugation to the trifluoroboronate moiety by standard synthetic organic chemistry techniques.

The trifluoroboronate moiety may likewise be prepared by standard synthetic techniques from commercially available starting materials. Examples of methods of synthesis for exemplary trifluoroboronate moieties comprising either an alkyne group or an azide group for conjugation with a somatostain analogue are provided in Examples 1 and 2 herein. While the trifluoroboronate moieties described in Examples 1 and 2 have been derivatized to allow for conjugation to an appropriately derivatized somatostatin analogue by click chemistry (as shown, for example, in FIG. 1), it will be readily apparent to those skilled in the art that other conjugation methods may be employed, for example, the use of NHS esters, maleimides, and the like, and appropriate trifluoroboronate moieties and somatostatin analogues may be prepared accordingly.

$^{18}$F Labelling

The fluorinated somatostatin derivatives can subsequently be labelled with $^{18}$F by simple isotope exchange using standard protocols (see, for example, Example 1). In certain embodiments, the isotope exchange may be carried out in a single reaction vessel with subsequent removal of excess fluoride ions by SPE, for example, on a Sep-Pak® or similar cartridge, without the need for HPLC purification.

Uses

Certain embodiments of the invention relate to the use of the fluorinated somatostatin derivatives, once labelled with $^{18}$F, as radiotracers. Some embodiments thus also relate to the use of the non-labelled fluorinated somatostatin derivatives in the preparation of radiotracers. In certain embodiments, the facile labelling of the fluorinated somatostatin derivatives by isotope exchange will allow for the radiotracers to be readily prepared on site in facilities, such as hospitals and clinics, which have access to a cyclotron for generation of $^{18}$F-fluoride.

As demonstrated herein, exemplary fluorinated somatostatin derivatives of general formula (I) exhibit high affinity for somatostatin receptors. Accordingly, when labelled with $^{18}$F, the fluorinated somatostatin derivatives of general formula (I) are useful for in vivo imaging applications, for example PET imaging applications, to image cells and tissues expressing somatostatin receptors including, but not limited to in vivo imaging of neuroendocrine tumours.

In some embodiments, $^{18}$F-labelled fluorinated somatostatin derivatives of general formula (I) may find use as PET imaging agents for imaging cancer, including cancers that express somatostatin receptors. Examples of such cancers, include but not limited to, neuroendocrine tumours, breast cancers, small cell lung cancer, lymphomas, meningiomas, pituitary adenomas and pancreatic cancer.

In some embodiments, it is contemplated that the fluorinated somatostatin derivatives of general formula (I), when the fluorine atoms are present as the $^{19}$F isotope, may find use as a therapeutic agents for treatment of diseases or disorders characterized by expression or overexpression of somatostatin receptors. Examples of such diseases or disorders include, but not limited to, neuroendocrine tumours, breast cancers, small cell lung cancer, lymphomas, meningiomas, pituitary adenomas and pancreatic cancer.

The fluorinated somatostatin derivatives of general formula (I) may also find use as research reagents, for example, in research into the role of somatostatin receptors in certain diseases or conditions.

Kits

As the fluorinated somatostatin derivatives of general formula (I) are generally stable and can be readily labelled in a single reaction vessel, certain embodiments of the invention relate to kits comprising a fluorinated somatostatin derivative of general formula (I) for the preparation of a radiolabelled tracer. The kit may also include instructions for use, which may be provided in paper form or in computer-readable form, such as a disc, CD, DVD or the like, and may further comprise a notice in the form prescribed by a governmental agency regulating the manufacture, use or sale of pharmaceuticals or biological products, which notice reflects approval by the agency of manufacture, for use or sale for human or animal administration.

The kit may comprise one or more containers containing a pre-determined amount of the fluorinated somatostatin derivative. Typically, the container will be a one that can be used directly in the isotope exchange reaction, for example, a vial or tube made of polypropylene or other suitable material. The amount of the fluorinated somatostatin derivative in each container may be an amount suitable to provide a single dose of the final radiolabelled tracer, or it may be an amount suitable to provide multiple doses of the radiolabelled tracer.

In certain embodiments, one or more of the components of the kit can be lyophilized and the kit can additionally contain a suitable solvent for reconstitution of the lyophilized components.

EXAMPLES

Example 1: Preclinical Evaluation of a High-Affinity $^{18}$F-Trifluoroborate Octreotate Derivative for Somatostatin Receptor Imaging Materials And Methods Reagents and solvents were purchased from Advanced Chemtech, Sigma-Aldrich, Combi-Blocks, or Novabiochem. The AR42J cell line was purchased from ATCC. $^{18}$F-fluoride Trap & Release Columns were purchased from ORTG Inc., and C18 Sep-Pak cartridges (1 cm$^3$, 50 mg) were obtained from Waters. An Endeavor 90 peptide synthesizer (Aapptec) was applied to synthesize the peptide. Electron-spray ionization low-resolution mass spectroscopy was performed on a Waters ZQ with a single quadrupole detector, attached to a Waters 2695 high-performance liquid chromatography (HPLC) column. All nuclear MR spectra were recorded at room temperature on a Bruker Avance 300 MHz spectrometer.

The following HPLC methods were used for purification and quality control. Method A: Agilent Eclipse XDB-C18 5-mm 9.2×250 mm semipreparative column; solvent A, 0.1% trifluoroacetic acid (TFA) water; solvent B, MeCN; 0-15 min, 20%-40% B; 15-20 min, 40%-20% B; flow rate, 4.5 mL/min; column temperature, 19° C.-21° C. Method B: Agilent Eclipse XDB-C18 5-mm 9.2×250 mm semipreparative column; solvent A, 0.1% TFA water; solvent B, MeCN; 0-2 min, 5%-20% B; 2-5 min, 20%-30% B; 5-20 min, 30%-50%; 20-22 min, 50%-5% B; flow rate, 3 mL/min; column temperature, 19° C.-21° C. Method C: Phenomenex Jupiter 10-mm C18 300-A° 4.6×250 mm analytic column; solvent A, 0.1% TFA water; solvent B, MeCN; 0-2 min, 5%-5% B; 2-7 min, 5%-20% B; 7-15 min, 20%-100%; 15-20 min, 100%-5% B; flow rate, 2 mL/min; column temperature, 19° C.-21° C.

To synthesize the precursor for labelling, a suitable TATE was first synthesized as previously described (Lewis J S, et al., Nucl Med Biol. 1999, 26:267-273) and converted to an azide derivative. The resin (Fmoc-Thr(tBu)-Wang) and growing chain were treated with 20% piperidine (1×5 min and 1×10 min) in N,N-dimethylformamide to remove the N$^\alpha$-Fmoc protecting group. The amino acids (3 equivalents [eq.] per coupling) Fmoc-Cys(Acm)OH, Fmoc-Thr(tBu)-OH, Fmoc-Lys(Boc)-OH, Fmoc-D-Trp(Boc)-OH, Fmoc-Tyr(tBu)-OH, and Fmoc-D-Phe-OH were subsequently coupled in nuclear matrix protein with the standard in situ activating reagent O-benzotriazole-N,N,N9,N9-tetramethyluronium-hexafluoro-phosphate (HBTU) (3 eq.) in the presence of diisopropylethylamine (6 eq.). Thallium (III) trifluoroacetate (2 eq.) in N,N-dimethylformamide deprotected the cysteines and concomitantly induced disulfide formation. Bromoaceticacid (40 eq.) was preactivated with diisopropylcarbodiimide (20 eq.) in dichloromethane for 10 min, filtered, and coupled to the N-terminus. NaN$_3$ (27.5 eq.) in dimethyl sulfoxide was added. The peptide was deprotected and simultaneously cleaved from the resin in 90:2.5:2.5:5 TFA:H$_2$O:triisopropylsilane:phenol for 4 h at room temperature. TATE-N$_3$ was purified by HPLC with a semipreparative column using method A to afford pure TATE-N$_3$ in quantities of about 10 mg. The calculated mass was 1,131.2, and the measured mass by electrospray ionization was 1,131.4. The purity of the peptide was greater than 99%.

N-propargyl-N,N-dimethyl-ammoniomethylboronylpinacolate (alkynyl-AMB(pin)) was first synthesized by condensation of iodomethylboronylpinacolate and propargylamine as previously described (Matteson D S, et al., J Organomet Chem. 1979, 170:259-264). Briefly, a dry round-bottomed flask was charged with N,N-dimethylpropargylamine (98 µL, 1.0 mmol) and 2 mL of anhydrous diethyl ether under argon, to which iodomethyl-boronylpinacolate (165 µL, 0.9 mmol) was added dropwise at room temperature. On stirring, the solution became cloudy and the desired product was collected as a white precipitate that was filtered and washed with cold Et$_2$O and then dried under high vacuum to give a fluffy white powder in 95% yield. $^1$H nuclear MR (300 MHz [Bruker], CD$_3$CN): d 4.40 (d, 2H), 3.31 (s, 2H), 3.22 (s, 6H), 3.21 (t, 1H), 1.27 (s, 12H); electrospray ionization: calculated, 224.1. found, 224.1.

Figure 10:
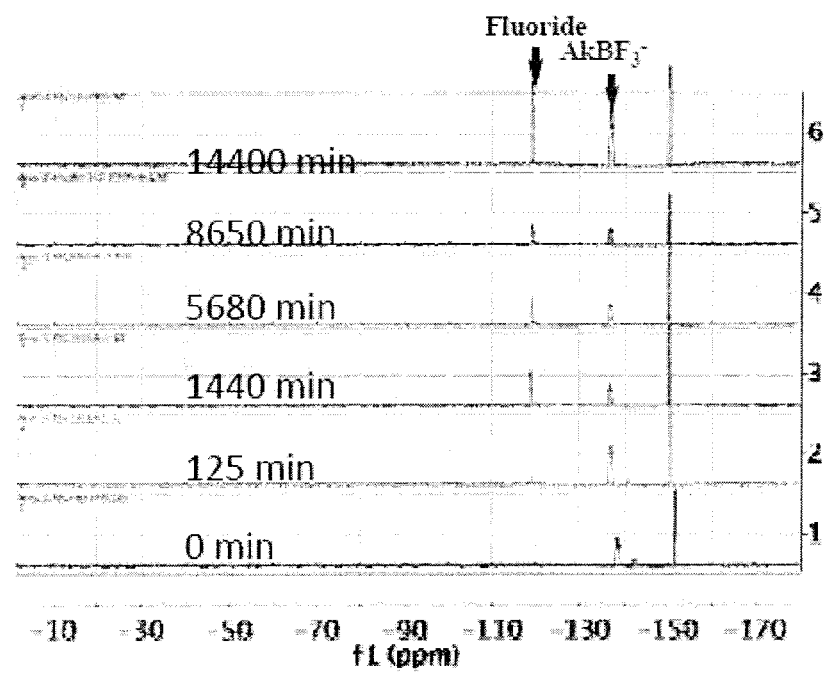
FIG. 10 shows (A) $^{19}F$-NMR kinetic analysis of the defluoridation from the $^{19}F$-$AMBF_3$ moiety ($^{19}F$-fluoride: 121 ppm relative to $CFCl_3$; $^{19}F$-$AMBF_3$: 137 ppm relative to $CFCl_3$), and (B) a plot of the relative $^{19}F$-NMR integration of the $^{19}F$-$PyBF_3$ as a function of all compounds ($^{19}F$-$AMBF_3$+$^{19}F$-fluoride) vs. time. Data are scaled 1000,000 min. Data were fit to a first-order reaction, and the half-life of the corresponding $^{19}F$-$AMBF_3$ was calculated to be 19,5000±500 min.
Figure 10:
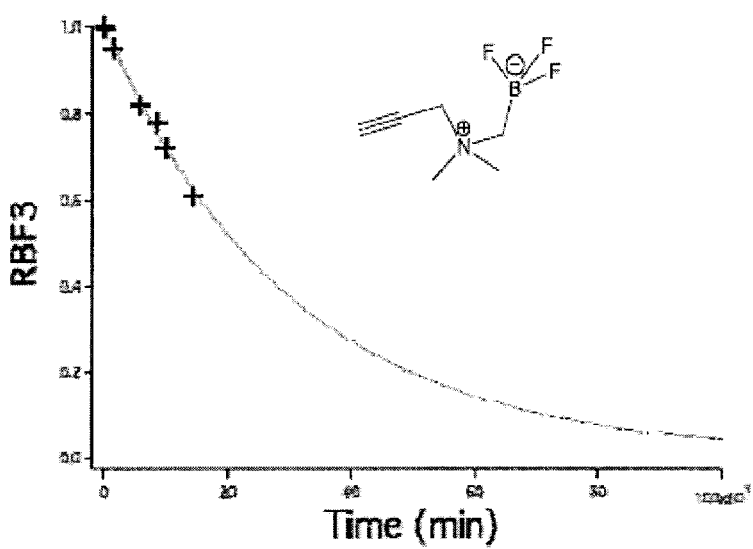

N-propargyl-N,N-dimethylammonio-methylboronylpinacolate (5.0 mg, 22.3 mol) was converted to the trifluoroborate (alkynyl-AMBF$_3$) through the addition of KHF$_2$ (3 M, 30 µL in water), HCl (4 M, 30 µL in water), deionized water (20 µL), and N,N-dimethylformamide (60 µL), 45° C., 2 h, and then quenched by NH$_4$OH (concentration, 10 µL). $^{19}$F NMR confirmed very slow solvolysis of the alkynyl-AMBF$_3$ (t$_{1/2}$: 13±0.3 days) (FIG. 10).

The crude reaction from preparation of the alkynyl-AMBF$_3$ above was directly used for click conjugation to TATE-azide without further purification: a mixture of TATE-azide (4.0 mg, 3.4 µmol), CuSO$_4$ (1.0 M, 5.0 µL), sodium ascorbate (1.0 M, 12.5 µL), and 5% NH$_4$OH (1:1 MeCN:H$_2$O, 50 µL) was added, and the mixture was heated to 45° C. for 2 h. Purification was performed with method B to isolate 2.3 mg of AMBF$_3$-TATE. Purity was confirmed with liquid chromatography-mass spectrometry (calculated, 1,296.5; obtained, 1,296.4). The purified $^{19}$F-AMBF$_3$-TATE was diluted in ethanol and portioned into aliquots of approximately 60 g (50 nmol) for radiolabelling in kit-like fashion.

Figure 2:
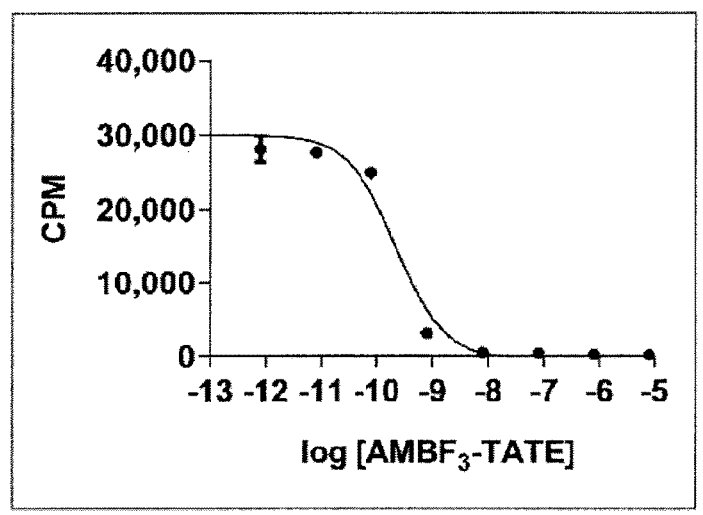
FIG. 2 presents the results from a representative example of competitive binding assay for $^{19}F$-$AMBF_3$-TATE; y-axis shows counts bound. Assay was run with triplicate data points. CPM=counts per minute.

After successful synthesis, the activity of $^{19}$F-AMBF$_3$-TATE was examined in vitro. Membranes from Chinese hamster ovary K1 cells transfected with sstr1, sstr2, sstr3, sstr5, and [$^{125}$I]-Tyr-somatostatin-14 were obtained from PerkinElmer. A standard filtration binding assay was performed in 96-well plates (MultiScreen; Millipore) to determine the binding affinities (inhibition constant, or K$_i$) of AMBF$_3$-TATE against different receptor subtypes. Briefly, membranes (0.25 L/well) were incubated with the $^{125}$I-labelled standard at a concentration of 0.05 nM for sstr2 or 0.2 nM for other subtypes. Increasing concentrations of AMBF$_3$-TATE were added to the wells in buffer (25 mM N-2-hydroxyethylpiperazine-N-2-ethanesulfonic acid, pH 7.4; 10 mM MgCl$_2$; 1 mM CaCl$_2$; and 0.5% bovine serum albumin). After incubation (37° C., 1 h), the wells were aspirated and washed 8 times with 50 mM ice-cold buffer (Tris-HCl, pH 7.4) over grade GF/B filters. The filters were removed and counted by a γ counter (Cobra II; Packard). A typical competition curve is shown in FIG. 2 (n=3). Data were fitted to a 1-site competition model (GraphPad Prism 6.1 software) to calculate K$_i$.

Figure 3:
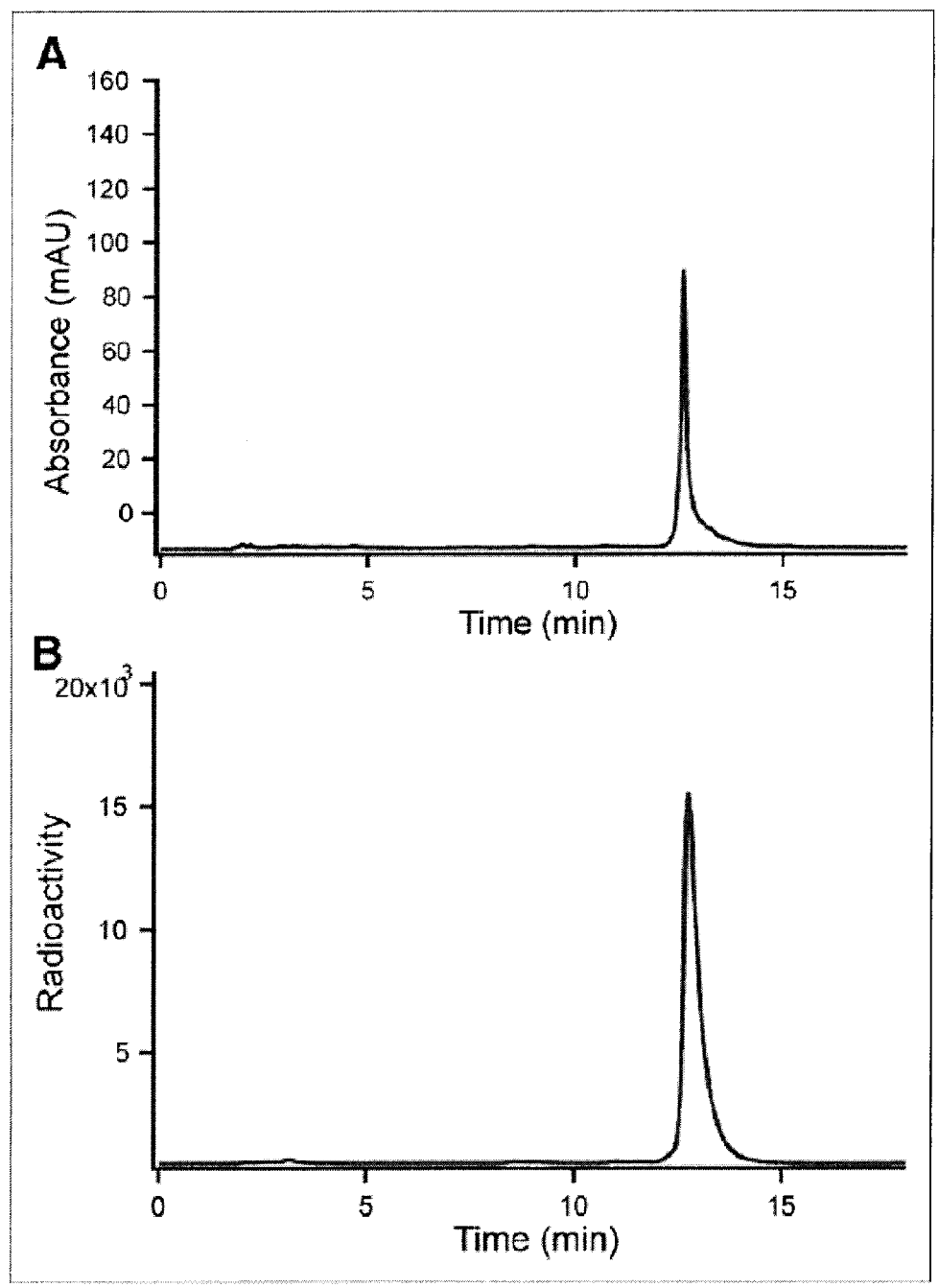
FIG. 3 shows HPLC traces of Sep-Pak-purified $^{18}F$-$AMBF_3$-TATE. (A) Ultraviolet trace measured at 277 nm. (B) Radioactivity trace. AU=arbitrary units.

For $^{18}$F labelling, AMBF$_3$-TATE (50 nmol) was resuspended in aqueous pyridazine-HCl buffer (~50 µL, pH 2) in a vial (polypropylene Falcon Tube; Corning) just before labelling. No-carrier-added $^{18}$-fluoride, 29.6-37 GBq (800-1,000 mCi), was obtained by bombardment of H$_2$$^{18}$O with 18-MeV protons, followed by trapping on an anion exchange resin (9 mg, quaternary ammonium, chloride form, prewashed with deionized water). The $^{18}$F-fluoride was eluted with 70-100 µL of isotonic saline into the reaction vial containing AMBF$_3$-TATE. The vial was placed in a heating block set at 80° C. for 20 min, whereupon the reaction was quenched by the injection of 2 mL of 5% NH$_4$OH in water. The reaction mixture was loaded onto a C18 light cartridge that was preconditioned by wetting with MeCN and washing with distilled water. Impurities (e.g., $^{18}$F-fluoride, pyridazine) were removed by flushing with 2 mL of saline. Radiochemically pure $^{18}$F-AMBF$_3$-TATE was released into a glass vial with 0.5 mL of 1:1 ethanol:saline to provide 7.4 GBq (200 mCi) of tracer. This solution was formulated in isotonic saline (5 mL). A small sample was removed for quality control analysis by HPLC with mass detection at 277 nm (FIG. 3).

Radiochemically pure $^{18}$F-AMBF$_3$-TATE, formulated in saline, was assayed for plasma stability. For this assay, 20 µL of $^{18}$F-AMBF$_3$-TATE were added to mouse plasma (500 µL) and incubated at 37° C. for 0, 60, and 120 min. After incubation at each time point, the reaction was quenched by adding 1 mL of MeCN to precipitate insoluble proteins from the solution. The quenched reactions were centrifuged to remove insoluble material. The supernatant was aspirated, filtered, and analyzed by HPLC using method C.

After labelling, imaging was undertaken. All animal studies were performed in accordance with the Canadian Council on Animal Care guidelines and were approved by the animal care committee of the University of British Columbia. Rat pancreatic adenocarcinoma cells (10$^7$ AR42J cells) were freshly expanded in a mixture of phosphate-buffered saline and Matrigel (Corning) and inoculated subcutaneously in female immunocompromised mice (NOD SCID [non-obese diabetic severe combined immunodeficient] IL2r-γ-null, bred in house). The tumours were grown for 2 wk until they reached 5-7 mm in diameter. While under 2% isoflurane anesthesia, the mice were injected via the tail vein with 0.37-0.74 MBq (10-20 µCi, 4-8 pmol) of $^{18}$F-AMBF$_3$-TATE (n=5). To demonstrate the specificity of in vivo uptake in receptor-positive tissues, 100 µg of $^{69/71}$Ga-DOTATATE were pre-injected 15 min before $^{18}$F-AMBF$_3$-TATE injection as a blocking control cohort (n=4). Sixty minutes after injection, the mice were anesthetized with isoflurane and euthanized by carbon dioxide. The organs were harvested, rinsed with saline, blotted dry, and collected in previously weighed tubes. The tubes containing the organs were counted in a Cobra-II γ counter. The tissue weight and associated count per minute were used to calculate the percentage injected dose per gram of tissue (% ID/g). Images were acquired using a multimodality PET/CT system (Inveon; Siemens).

Approximately 3.7 MBq (100 µCi, ~40 pmol) of radiotracer were injected in the caudal lateral tail vein of tumour-bearing mice. Sixty minutes after radiotracer injection, the animals were anesthetized with isoflurane inhalation and a baseline low-dose CT scan was obtained for localization and attenuation correction, followed by a static PET scan acquired for 10 min. The mice were kept warm by a heated pad on the scanner bed during acquisition. $^{69/71}$Ga-DOTATATE (100 µg per mouse) was pre-injected as a blocking agent. The images were reconstructed by an iterative reconstruction algorithm (3-dimensional ordered-subsets expectation maximization/maximum a posteriori) using the Inveon Acquisition Workplace Software (Siemens), applying normalization, dead time, random, and attenuation corrections. Uptake into tumour and tissues of interest was determined by regions of interest, and % ID/g was calculated (assuming a tissue density of 1.0 g/cm$^3$). The mean % ID/g was calculated from a region of interest that matched the tumour contours on CT. The peak % ID/g was calculated from the hottest 2×2 voxel cluster within the tumour. In 1 animal, a dynamic scan was acquired in list mode for 60 min under continuous isoflurane inhalation, starting concurrently with radiotracer injection. Imaging data from this mouse were not combined with the results of static imaging and were used to obtain the tissue time-activity curves reported in FIG. 4.

Results

In Vitro Affinity

The K$_i$ of AMBF$_3$-TATE using human sstr2 receptors expressed on Chinese hamster ovary membranes was 0.13±0.03 nM. Using identical assay conditions and the same lot of membranes, the K$_i$ for gallium-DOTATATE was 0.7±0.2 nM. A representative competitive binding assay curve is shown in FIG. 2. No significant displacement of binding to sstr1 was observed. The inhibition constants for sstr3 and sstr5 were 28.4±8.6 nM and 11.35±2.8 nM, respectively.

Radiosynthesis

Figure 5:
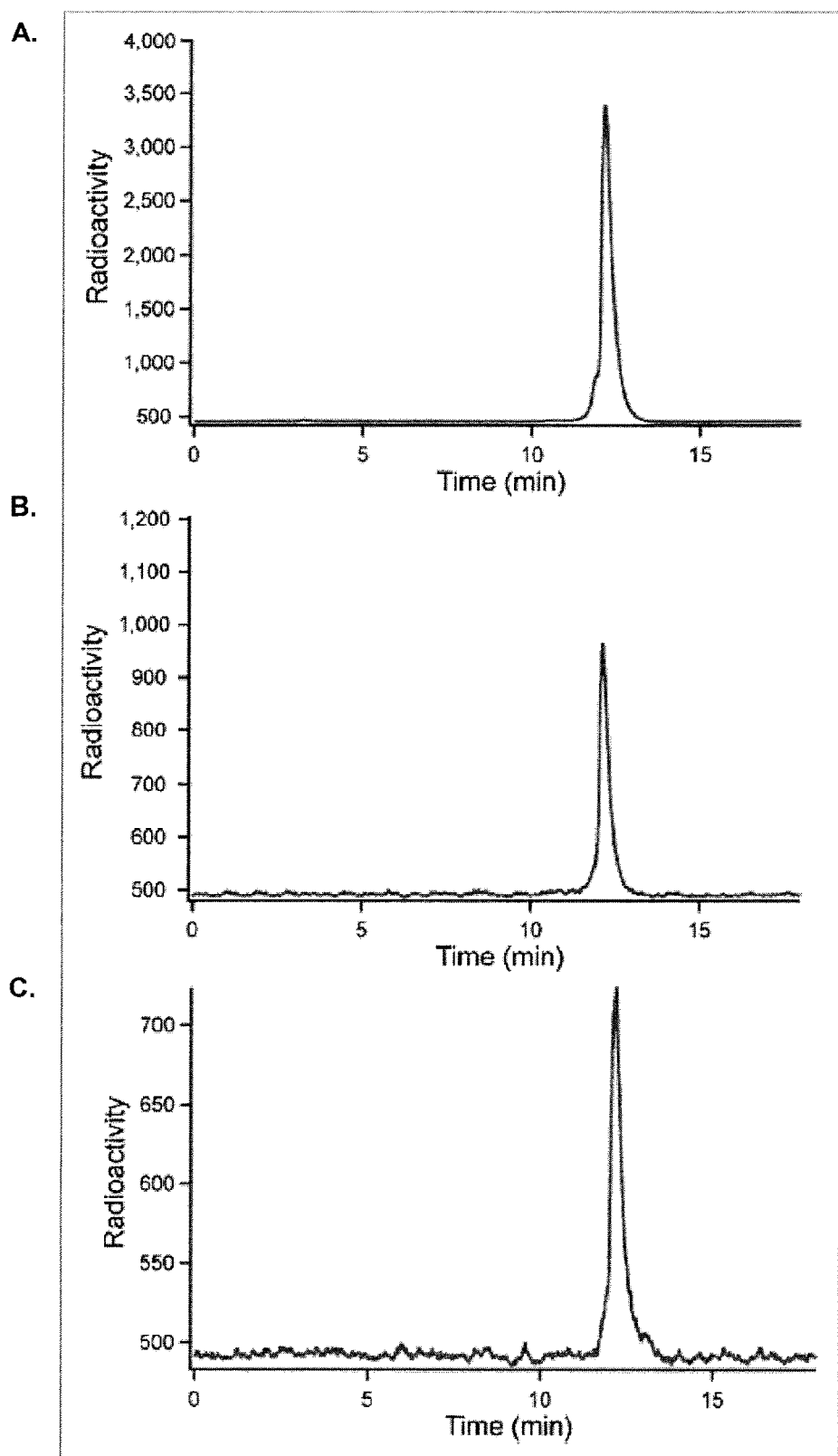
FIG. 5 depicts the results of a plasma stability assay of $^{18}F$-$AMBF_3$-TATE; radiotraces are shown for 0, 60, and 120 min.

Starting with 29.6-37 GBq of no-carrier-added $^{18}$F-fluoride (800-1,000 mCi), approximately 7.4 GBq of $^{18}$F-AMBF$_3$-TATE were obtained within 25 min (24%±4%, n=5) and reinjected into HPLC for quality analysis (FIG. 3), which showed a single peak in both radioactive and ultraviolet modes. Because approximately 7.4 GBq (~200 µCi) of 2 were obtained starting with 50 nmol of precursor, the specific activity was 148 GBq/µmol (3 Ci/µmol), with a radiochemical yield of 20%-25% (not corrected for decay). To validate this calculation, a standard curve showed that the specific activity was more than 111 GBq/µmol (0.3 Ci/µmol). $^{18}$F-AMBF$_3$-TATE was incubated in mouse plasma for 120 min with no detectable decomposition (FIG. 5).

PET/CT Imaging

Figure 6:
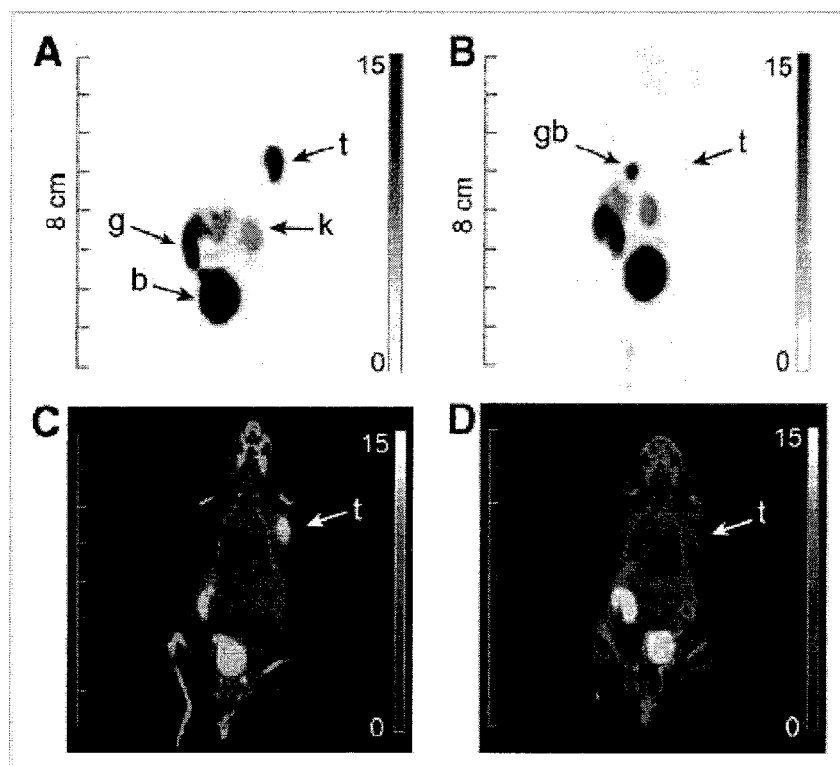
FIG. 6 shows $^{18}F$-$AMBF_3$-TATE PET images of AR42J tumour-bearing mice at 60 min after injection: unblocked (A and C) and blocked (B and D). Upper panels are maximum-intensity-projection images; bottom panels are corresponding fused coronal images. Color bars are calibrated in % ID/g with no background subtracted. Tracer specifically accumulated into tumour (t), whereas remainder rapidly cleared via kidneys (k) to bladder (b). Some gut (g) and gallbladder (gb) accumulation occurred because of rapid hepatobiliary excretion.

Uptake in the AR42J tumours was intense and clearly specific as evidenced by the lack of uptake in the tumours of mice receiving unlabelled competitor (FIG. 6). The average of the tumour uptake based on the whole tumour region of interest was 10.2±2.1% ID/g. The average of the peak tumour uptake based on the hottest voxel cluster was 23.6±3.0% ID/g. In contrast, the average uptake in the liver, blood pool, and muscle was 0.83±0.16, 0.47±0.12, and 0.09±0.03% ID/g, respectively. Excretion was predominantly renal, with significant clearance to the bladder and low kidney retention. Some hepatobiliary tract excretion was notably rapid, leading to high tumour-to-liver ratios. Bone uptake was undetectable, and there was low background activity in blood and muscle, resulting in high-contrast images.

Pharmacokinetics (Time—Activity Curve Analysis)

Figure 4:
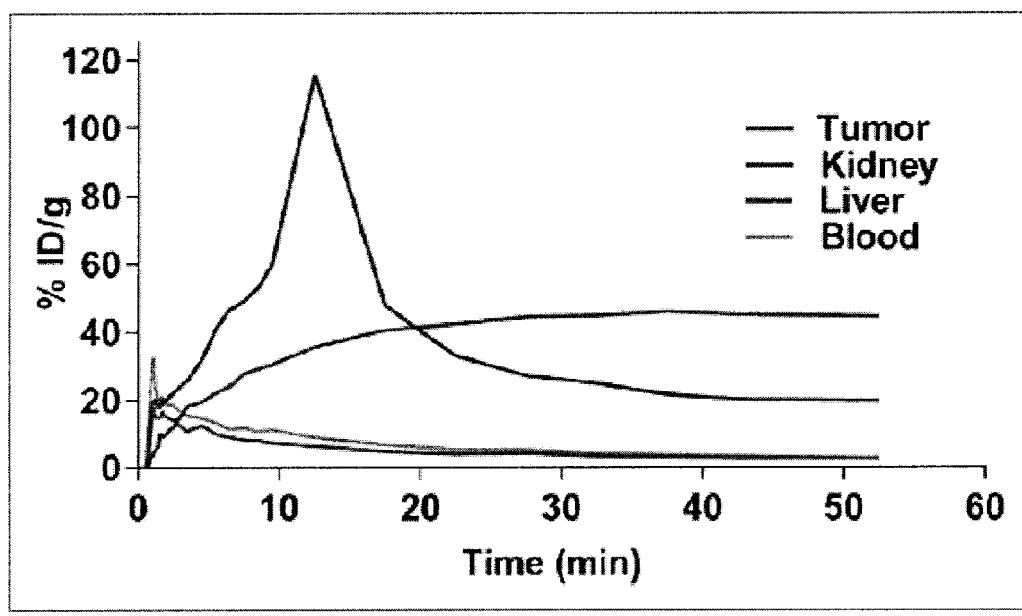
FIG. 4 presents time-activity curves indicating blood, liver, and kidney clearance and peak tumour uptake (from hottest voxel cluster in tumour from a single mouse) for $^{18}F$-$AMBF_3$-TATE.

Time-activity curves of uptake in tumour and other tissues from a tumour-bearing mouse are presented in FIG. 4. Time-dependent tumour uptake increased to a peak voxel cluster value of approximately 40% ID/g in a mouse with a fairly large tumour. Uptake in non-target tissues rapidly declined after reaching the peak value at a time point soon after intravenous administration.

Biodistribution Studies

Figure 7:
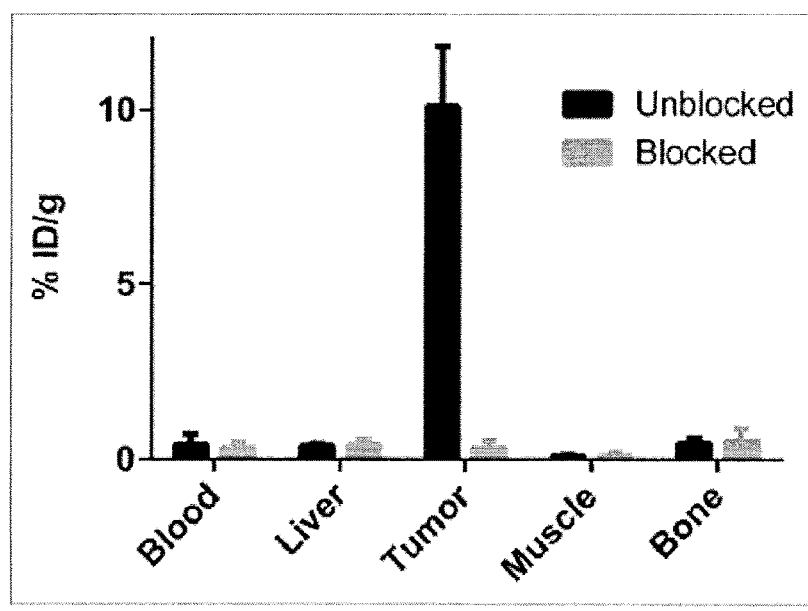
FIG. 7 shows relative uptake of $^{18}F$-$AMBF_3$-TATE into selected organs at 60 min after injection in AR42J-bearing mice, and demonstrates high receptor-mediated uptake in tumours compared with normal tissues.

The ex vivo biodistribution data of $^{18}$F-AMBF$_3$-TATE at 1 h (see Table 1) corroborate the scanning data. The relative uptake values in representative tissues are shown in FIG. 7. Uptake in AR42J xenograft tumours in the unblocked mice was 10.11±1.67% ID/g. As expected, excess competitor caused a substantial reduction in tumour uptake: 0.32±0.21% ID/g. Hence, blocking efficiency was 97%. Uptake values in blood and muscle were low: 0.40±0.31% ID/g and 0.11±0.03% ID/g, respectively, which gave high tumour-to-blood and tumour-to-muscle ratios of 25.1±1.0 and 89.0±3.1, respectively. Bone uptake was negligible (0.46±0.17% ID/g), indicating no in vivo defluorination.

TABLE 1

Biodistribution of $^{18}$F-AMBF$_3$-TATA (% ID/g)

| Tissues | Unblocked | | Blocked | |
|---|---|---|---|---|
| | Average | SD | Average | SD |
| Blood | 0.40 | 0.31 | 0.32 | 0.15 |
| Plasma | 0.72 | 0.71 | 0.92 | 0.16 |
| Uterus | 0.26 | 0.05 | 0.51 | 0.11 |
| Large intestine | 2.28 | 2.64 | 4.27 | 6.20 |
| Small intestine | 3.23 | 1.58 | 1.82 | 1.70 |
| Spleen | 0.42 | 0.19 | 0.31 | 0.11 |
| Liver | 0.39 | 0.05 | 0.41 | 0.14 |
| Pancreas | 2.81 | 1.49 | 0.20 | 0.01 |
| Adrenal glands | 0.54 | 0.18 | 0.28 | 0.07 |
| Kidney | 4.90 | 1.54 | 4.50 | 3.54 |
| Lungs | 1.85 | 0.83 | 0.79 | 0.26 |
| Heart | 0.17 | 0.05 | 0.88 | 1.12 |
| Tumour | 10.11 | 1.67 | 0.32 | 0.21 |
| Muscle | 0.11 | 0.03 | 0.11 | 0.09 |
| Bone | 0.46 | 0.17 | 0.54 | 0.36 |
| Brain | 0.03 | 0.01 | 0.22 | 0.33 |
| Tail | 0.28 | 0.06 | 0.38 | 0.09 |

Discussion

Isotope exchange on the organotrifluoroborate prosthetic greatly simplified labelling on several accounts. First, only submilligram quantities of precursor were needed for labelling. Second, no time-consuming azeotropic fluoride drying was required, because no-carrier-added $^{18}$F-fluoride was eluted in isotonic saline and used directly for an aqueous labelling reaction. Third, labelling was rapid (~20 min) and provided for high specific activity. Fourth, because the precursor is chemically identical to the product, time-consuming HPLC purification was obviated in favor of a simple C18 Sep-Pak elution to remove free fluoride. Besides the methodologic simplicity, the yields provide multiple human doses in a single run. In light of improvements in cyclotron output to provide multiple-curie levels of $^{18}$F-fluoride (Eberl S, et al., Appl Radiat Isot. 2012, 70:922-930), this methodology is readily applicable to existing production facilities. Moreover, the simplicity of the process should be easily amenable to automation and microfluidic flow technologies.

Whereas good radiosynthetic attributes are a prerequisite for use, the real value of a given tracer ultimately lies in the in vivo image data and corroborating biodistribution data. There is an extensive body of literature detailing the labelling and imaging of various TATE analogues by SPECT or PET. A brief comparison of the representative radiolabelled TATE derivatives is featured in Table 2. Comparison of receptor binding affinities is difficult because many authors report an inhibitory concentration of 50%, which is dependent on assay conditions. Among the published TATE-based radiotracers, gallium-DOTATATE has the highest affinity for sstr2 reported to date. Under identical conditions, $^{18}$F-AMBF$_3$-TATE showed higher affinity than gallium-DOTATATE. This finding was both unanticipated and significant. The sensitivity of somatostatin analogues, either agonists or antagonists, to substitutions at the N-terminus and to the radiometal is well documented (Fani M, et al., J Nucl Med. 2012, 53:1481-1489; Reubi J C, et al., Eur J Nucl Med. 2000, 27:273-282). In the present Example, the octreotate was modified with the AMBF$_3$ prosthetic via copper-catalyzed click conjugation, and a decrease in the binding affinity to the sstr2 was expected. Instead, a more than 5-fold higher binding affinity than for $^{68}$Ga-DOTATATE as assayed under identical conditions was observed.

TABLE 2

Comparison of Some Octreotide and Octreotate Derivatives

| Ligand | Synthesis Time (min) | Specific Activity (GBq/μmol) | HPLC Purification | Tumour Type | Tumour % ID/g |
|---|---|---|---|---|---|
| $^{111}$In-DTPA-pentetreotide[1] | >60 | 44.2 | No | AR42J | 0.99* |
| $^{99m}$Tc-depreotide[1] | 20 | 37 | No | CA20948 | 4.81§ |
| $^{111}$In-DOTA-TATE[2] | >60 | 15.9 | No | AR42J | 4.12* |
| $^{99m}$Tc-EDDA/HYNIC-TATE[2] | 20 | 60 | No | AR42J | 5.01 |
| $^{64}$Cu-TE1A1P-Y3-TATE[3] | >60 | 48 | No | AR42J | 5.11 |
| $^{18}$F-FETE-PEG-TOCA[4] | 90 | 5.9 | Yes | AR42J | 5.14 |
| $^{18}$F-FET-bAG-TOCA[4] | 90 | 3.9 | Yes | AR42J | 8.23 |
| $^{18}$F-FET-bAG-[W-c-K][4] | 90 | 12.3 | Yes | AR42J | 0.11 |
| $^{18}$F-AIF-NOTA-OC[5] | 45 | 36.1 | No | AR42J | 6.43 |
| $^{18}$F-SiFA-Tyr$^3$-OC[6] | <30 | 29-56 | No | AR42J | 7.73 |
| $^{68}$Ga-DOTA-TATE[7] | 45 | Not given | No | AR42J | 2.75 |
| $^{18}$F-AMBF$_3$-TATE | <30 | 111 | No | AR42J | 10.11 |

*4-h time point
§90-min time point
[1]Vallabhajosula S, et al., J Nucl Med. 1996, 37:1016-1022;
[2]Storch D, et al., J Nucl Med. 2005, 46: 1561-1569;
[3]Guo Y, et al., Bioconjug Chem. 2012, 23: 1470-1477;
[4]Leyton J, et al., J Nucl Med. 2011, 52: 1441-1448;
[5]Laverman P, et al., J Nucl Med. 2010, 51: 454-461;
[6]Wängler C, et al., Bioconjug Chem. 2010, 21: 2289-2296;
[7]Poeppel T D, et al., J Nucl Med. 2011, 52: 1864-1870.

The inhibition constants to sstr3 and sstr5 also appeared to be lower than the values published for Ga-DOTATATE, suggesting that other zwitterionic moieties at the N-terminus may improve affinity. On the basis of PET/CT imaging, $^{18}$F-AMBF$_3$-TATE exhibited low background activity in non-target tissues and high receptor-mediated uptake in a preclinical murine model of sstr2-positive cancer. Corroborating the in vivo imaging data, ex vivo biodistribution verified the high tumour uptake values. Although liver uptake of radiometallated octreotides typically is low, this is not always the case for $^{18}$F-labelled octreotides. Liver uptake, and in particular nonspecific uptake, is often observed and may preclude clinical detection of liver metastasis. Interestingly, the liver uptake of $^{18}$F-AMBF$_3$-TATE was low, resulting in a higher tumour-to-liver ratio (26.21±0.79 1 h after injection) than has been reported for other $^{18}$F-labelled TATE analogues (0.25-5.0 2 h after injection) (Leyton J, et al., J Nucl Med. 2011, 52:1441-1448; Wangler C, et al., Bioconjug Chem. 2010, 21:2289-2296).

A plasma stability assay (37° C.) showed negligible decomposition of $^{18}$F-AMBF$_3$-TATE after 120 min. Consistent with this finding, minimal bone uptake was observed in both PET/CT and biodistribution, resulting in a high tumour-to-bone ratio of up to 21.3±3.6. This low, nonspecific bone uptake is particularly encouraging for the detection of bone metastasis.

Conclusions

This Example reports high-affinity octreotate-organotrifluoroborate conjugate that was radiolabelled with $^{18}$F in high yield and high specific activity via a facile isotope exchange reaction using minute quantities of precursor peptide, without HPLC purification. This methodology provides for rapid, multi-dose tracer production in a single run that should be amenable to automation. In addition to radiosynthetic ease, the biologic evaluation of $^{18}$F-AMBF$_3$-TATE indicated that this tracer provides good stability, optimal pharmacokinetics, excellent binding affinity, and high tumour-to-nontarget-tissue ratios for in vivo imaging.

Example 2: Preparation of Azidoethyl-AMBF$_3$

Azidoethyl-AMBF$_3$ (compound 5) was prepared as shown generally in Scheme 1:

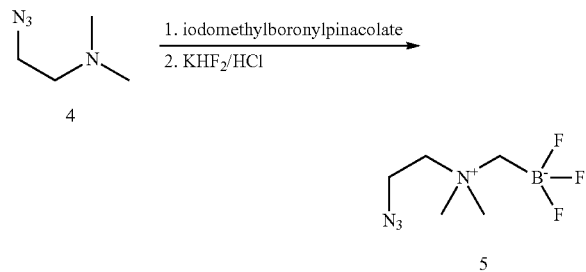

Scheme 1

N,N-dimethyl-2-azidoethylamine 4 (114 mg, 1.0 mmol) was dissolved in anhydrous diethyl ether (5 mL) in a flame-dried round bottom flask. At room temperature, iodomethylboronyl pinacolate (182 µL, 1.0 mmol) was added drop-wise over 5 min. The alkylated product precipitated as a fluffy white powder, which was separated by filtration and dried under vacuum. The pincaolate was then converted to the corresponding trifluoroborate through the addition of KHF$_2$ (3 M, 300 µL in water) and HCl (4M, 300 µL in water) along with deionized water (200 µL) and DMF (600 µL) at 45° C. for 2 hours, and then quenched by NH$_4$OH (conc., 10 µL). Free fluoride was removed by passing the reaction mixture through silica gel to give compound 5. ESI: [M–F]$^+$ calculated: 177.09; obtained: 177.1; HRMS [M$^+$]: calculated: 218.1041. found: 218.1041. Compound 5 was used without further purification for condensation with peptides.

Example 3: Kit-Like Labelling of AMBF$_3$-Bioconjugates

Figure 9:
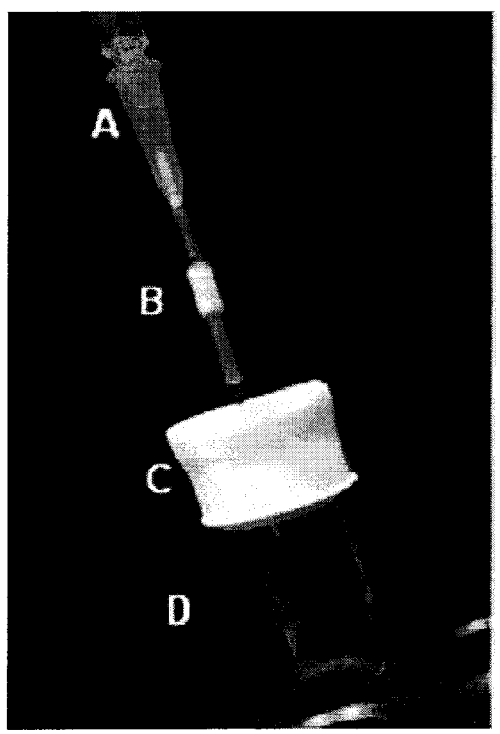
FIG. 9 shows an example of a no carrier added (NCA) [$^{18}F$]fluoride ion elution trap and single reaction vessel for isotope exchange. A: 16-gauge needle where the needle has been cut; B: anion-exchange cartridge containing 9 mg of standard QMA resin fitted with the remaining needle point; C: standard rubber septum; D: in temp block: polypropylene vial (sawed-off Falcon tube) that contains $AMBF_3$ precursor. NCA [$^{18}F$]fluoride ion is trapped on the cartridge, which is then inserted into the septum. The [$^{18}F$]fluoride ion is eluted with 60 μL isotonic saline into the tube D in which labelling proceeds. All events occur within a fully shielded hot-cell.

For labelling, a wet NCA (no carrier added) solution of [$^{18}$F]fluoride ion was used directly following trapping. Using disposable labware, a very small QMA cartridge (9 mg resin) was affixed to the reaction vessel (10 mL polypropylene conical tube), as shown in FIG. 9. The very small QMA column efficiently traps Curie levels of NCA [$^{18}$F] fluoride ion, which was directly eluted with <60 µL saline into the reaction vessel containing the AMBF$_3$-bioconjugate to be labelled by isotope exchange (IEX). Once mixed (10 s), the reaction vessel was placed in a heating block at 80° C. After 15 min, the reaction was quenched with 2 mL PBS or 2 mL NH$_4$OH and the entire reaction mixture was directly loaded onto a C18 Sep-Pak column. Following water wash (5 mL) the labelled compound was eluted into PBS/ethanol (2 mL).

Example 4: Preparation and Testing of AMBF$_3$-LM3

Synthesis of azidoacetyl-LM3

Azidoacetyl-LM3 was synthesized via the N$^\alpha$-Fmoc solid-phase peptide synthesis strategy starting from D-Tyr-Rink Amide MBHA resin. The resin was treated with 20% piperidine in DMF to remove the N$^\alpha$-Fmoc protecting group. The following Fmoc-protected amino acids (3 equivalents) including Fmoc-Cys(Acm)-OH, Fmoc-Thr(tBu)-OH, Fmoc-Lys(Boc)-OH, Fmoc-D-Phe(Cbm)-OH, Fmoc-Tyr(tBu)-OH, Fmoc-D-Cys(Acm)-OH, Fmoc-Cl-Phe-OH were subsequently coupled to the sequence in correct order. The coupling was carried out in NMP with standard in situ activating reagent HBTU/HOBT (3 equivalents) in the presence of DIEA (6 equivalents). Cyclization was performed by incubation of the resin with 2 equivalents of thallium(III) trifluoroacetate in DMF at room temperature for 90 min. Bromoacetic acid (40 equivalents) was pre-activated with DIC (20 equivalents) in DCM for 10 min, filtered, and then coupled to the peptide sequence. Finally, the resin was treated with sodium azide (27.5 equivalents) in DMSO to provide the azide functional group at the N-terminus for click reaction.

The peptide was de-protected and simultaneously cleaved from the resin by the treatment of a cocktail of trifluoroacetic acid/water/triisopropylsilane (95:2.5:2.5). After filtration, the peptide was precipitated by the addition of cold diethyl ether to the TFA solution. The crude product was filtered, dried, and purified by HPLC (Luna C18 semi-prep column, 4.5 mL/min, 20-35% MeCN (0.1% TFA) in Water (0.1% TFA) in 30 min, RT=30). Azidoacetyl-LM3 was obtained in 15% yield. ESI-MS: calculated for Azidoacetyl-LM3 C$_{55}$H$_{68}$ClN$_{15}$O$_{13}$S$_2$ 1245.4. found [M+H]$^+$ 1246.9.

Synthesis of AMBF$_3$-LM3

Figure 8:
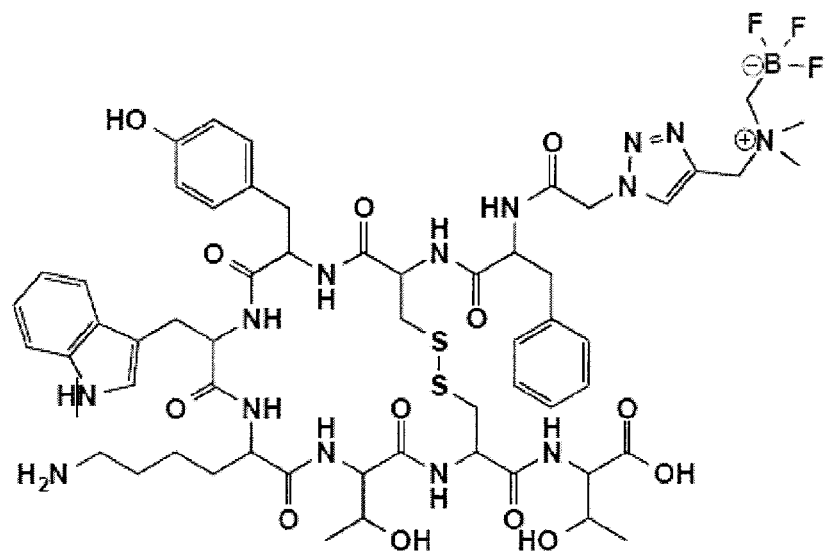
FIG. 8 shows the chemical structures of $AMBF_3$-TATE (2), $AMBF_3$-LM3 (3), $AMBF_3$-TOC (6) and $AMBF_3$-JR11 (7).
Figure 8:
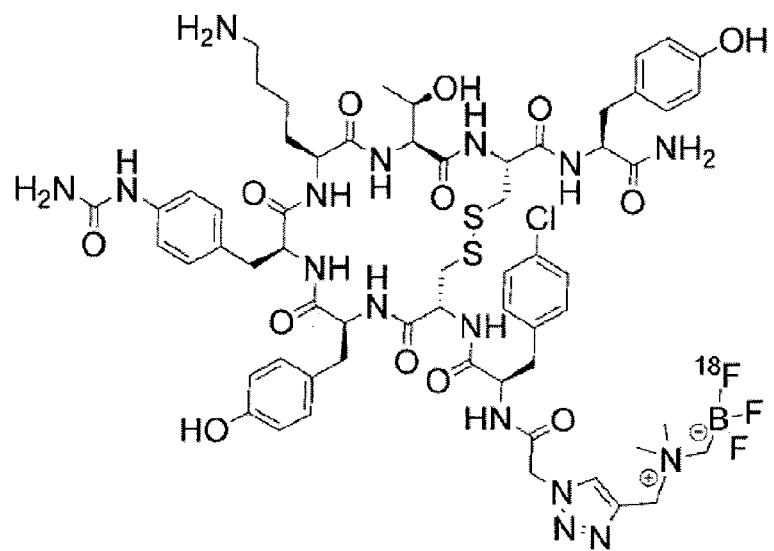

Propargyl-AMBF$_3$ (compound 1, FIG. 1) was prepared as described in Example 1, and conjugated to azidoacetyl-LM3 as described in Example 1 for TATE-azide to give AMBF$_3$-LM3 (compound 3, FIG. 8). Labelling as described in Example 3 gave radiochemically pure $^{18}$F-AMBF$_3$-LM3 (ca. 200 mCi) in 20 min in comparable yields to AMBF$_3$-TATE at high specific activity (ca. 3 Ci µmol$^{-1}$). $^{18}$F-AMBF$_3$-LM3 also showed specific and very high tumour uptake in AR42J pancreatic xenograft tumours in mice. Unbound tracer cleared rapidly through the kidneys with minimal uptake in liver and negligible uptake in bone.

Example 5: Preparation of AMBF$_3$-TOC

Synthesis of azidoacetyl-TOC

Azidoacetyl-TOC was synthesized via the N$^\alpha$-Fmoc solid-phase peptide synthesis strategy starting from H-Threoninol(But)-2-ClTrt resin. The following Fmoc-protected amino acids (3 equivalents) including Fmoc-Cys (Acm)-OH, Fmoc-Thr(tBu)-OH, Fmoc-Lys(Boc)-OH, Fmoc-D-Trp(Boc)-OH, Fmoc-Tyr(tBu)-OH, Fmoc-Cys (Acm)-OH, Fmoc-D-Phe-OH were subsequently coupled to the sequence in correct order. The coupling was carried out in NMP with the standard in situ activating reagent HBTU/HOBT (3 equivalents) in the presence of DIEA (6 equivalents). Cyclization was performed by incubation of the resin with 2 equivalents of thallium (III) trifluoroacetate in DMF at room temperature for 90 min. Finally, azidoacetic acid (10 equivalents) was pre-activated with DIC (5 equivalents) in DCM for 10 min, filtered, and then coupled to the peptide sequence to provide the azide functional group at the N-terminus for the subsequent click reaction. The peptide was de-protected and simultaneously cleaved from the resin by the treatment with a mixture of trifluoroacetic acid:water:triisopropylsilane (95:2.5:2.5). After filtration, the peptide was precipitated by the addition of cold diethyl ether to the TFA solution. The crude product was filtered, dried, and purified by HPLC (Luna C18 semi-prep column, 4.5 mL/min, 30% MeCN (0.1% TFA) in water (0.1% TFA), RT=18). Azidoacetyl-TOC was obtained in 16% yield. ESI-MS: calculated for azidoacetyl-TOC $C_{51}H_{67}N_{13}O_{12}S_2$ 1117.45. found [M+H]$^+$ 1118.0.

Synthesis of AMBF$_3$-TOC

An Eppendorf tube (1.5 mL) was charged with a mixture of N-propargyl-N,N-dimethylammonio-methyltrifluoroborate (1.03 mg, 6.3 µmol), CuSO$_4$ (1.0 M, 5.0 µL), sodium ascorbate (1.0 M, 12.5 µL), 5% NH$_4$OH (MeCN/H$_2$O=1:1, 50 µL) and azidoacetyl-TOC (3.5 mg, 3.13 µmol). The mixture was warmed up to 45° C. for 2 h. Purification was performed by HPLC using the following conditions: Luna C18 semi-prep column, 4.5 mL/min, 26% MeCN (0.1% TFA) in water (0.1% TFA), RT=17, to isolate 3.6 mg of AMBF$_3$-TOC (compound 6, FIG. 8) (54%). ESI-MS: calculated for AMBF$_3$-TOC $C_{57}H_{78}BF_3N_{14}O_{12}S_2$ 1282.5. found [M+H]$^+$ 1283.6.

Radiolabelling $^{19}$F-AMBF$_3$-TOC (100 nmol) was dissolved in a mixture of aqueous pyridazine-HCl buffer (12 µL, 1M, pH=2) and DMF (15 µL) in a 6-mL Falcon tube. No carrier-added $^{18}$F-fluoride was obtained by bombarding H$_2$$^{18}$O with 18 MeV protons, followed by trapping on a $^{18}$F-fluoride Trap & Release Column. The $^{18}$F-fluoride was eluted from the column with 70 µL saline into the Falcon tube containing $^{19}$F-AMBF$_3$-TOC. The tube was placed in a heating block and heated at 70° C. for 20 min. The reaction mixture was subsequently quenched with 5% aqueous NH$_4$OH (2 mL), and loaded onto a C18 light Sep-Pak cartridge. Free $^{18}$F-fluoride was removed by washing the Sep-Pak cartridge with deionized water (2 mL×2). $^{18}$F-AMBF$_3$-TOC was then eluted from the cartridge with 9:1 ethanol:saline (0.4 mL), and diluted with saline for in vitro plasma stability, biodistribution and PET/CT imaging studies. A small sample was removed for quality control analysis by HPLC (Luna C18 semi-prep column, 4.5 mL/min, 26% MeCN (0.1% TFA) in water (0.1% TFA), RT=18). The decay-corrected radiochemical yield was 17±1% and radiochemical purity was 94±2% (n=3). The Log D (7.4) of $^{18}$F-AMBF$_3$-TOC was −1.6±0.01.

The stability of $^{18}$F-AMBF$_3$-TOC was assessed in mouse plasma and analyzed by HPLC as described in Example 1. More than 88% and 63% of $^{18}$F-AMBF$_3$-TOC remained intact after 1 h and 2 h incubation at 37° C., respectively.

Example 6: Evaluation of Binding, Biodistribution and PET/CT Imaging with AMBF$_3$-TOC Methods
In Vitro Competition Binding Assays The binding affinity of AMBF$_3$-TOC was analysed in vitro using competitive binding assays. Purified membranes from Chinese hamster ovary K1 cells transfected with sstr2a (Perkin Elmer) were co-incubated with [$^{125}$I]-Tyr$^{11}$-somatostatin-14 (Perkin Elmer) at increasing concentrations of BF$_3$-TOC. The assay was performed in a 96-well filter plate (Millipore) with a 1.2 µL pore size. Each well contained 0.213 µg of membrane, 0.05 nM of radioligand and various concentrations of BF$_3$-TOC ($10^{-13}$ to $10^{-5}$ M) all dissolved in buffer (25 mM 4-(2-hydroxyethyl)-1-piperazineethanesulfonic acid, pH 7.4, 10 mM MgCl$_2$, 1 mM CaCl$_2$, 0.5% BSA) and incubated for 60 min at 27° C. After incubation, wells were aspirated and washed 6 times with 200 µL wash buffer (50 mM Tris-HCl pH 7.4, 0.2% BSA). Filters were removed and counted in a 2480 Automatic Gamma counter (Perkin Elmer). The inhibition constant (Ki) was calculated by fitting data to a 1-site competition model (GraphPad Prism 6.05). All samples were performed in triplicates (n=3).

In Vivo Studies: Biodistribution and PET/CT Imaging

All animal studies were done in accordance with the Canadian council on animal care guidelines and approved by the animal care committee at the University of British Columbia. Tumour-bearing NOD scid gamma (NSG) mice (bread in house) were used for PET/CT imaging (n=2) and biodistribution (n=4). 6-11 days prior to tumour inoculation, slow release estrogen pellets (17 β-estradiol, IRA) were implanted subcutaneously on the posterior of mice, accompanied with Metacam (Boehringer Ingelheim) analgesia at a dose of 2 mg/kg. Metacam was further administered at 1 mg/kg once a day for the following two days. Cells from the ZR-75-1 breast cancer model were implanted subcutaneously on the right shoulder and grown 5-6 weeks until tumours were 100-300 mm$^3$. A total of 3.3×10$^6$ cells were implanted in a 1:1 solution of matrigel (Corning) and phosphate buffered saline (total volume=100 µL).

The mice used for PET/CT imaging (n=2) were sedated with 2% isoflurane prior to receiving a [$^{18}$F]-BF$_3$-TOC radiotracer injection of 5.77-7.28 MBq (577-728 µCi) via the lateral tail vain. They were allowed to recover and given approximately 40 minutes of uptake time, until they were sedated once again and placed in the scanner. A baseline CT scan was obtained prior to PET for localization and attenuation correction. Subsequently, a 10 minute single static emission PET scan was acquired exactly 60 minutes post injection. The scanner bed was heated to maintain mouse body temperature at 37° C. At the end of the scan, mice were euthanized via carbon dioxide asphyxiation. Blood was promptly extracted using cardiac puncture and organs were harvested, weighted and counted in a 2480 Automatic Gamma counter (Perkin Elmer) for biodistribution studies. Additionally, two extra mice were used for biodistribution alone, receiving 1.03-1.71 MBq (103-171 µCi) of activity. They were sacrificed 75 min post-injection and organs were harvested the same way. The weight of the tissue and its associated counts-per minute was used to calculate injected dose per gram (% ID/g).

PET/CT images were further analysed for tissue uptake, also in % ID/g. Regions of interest (ROIs) were drawn based on the CT image and transferred the PET image. The peak % ID/g was calculated from the hottest 2×2 voxel cluster in the respective ROI.

Results

In Vitro Binding Assay

Figure 11:
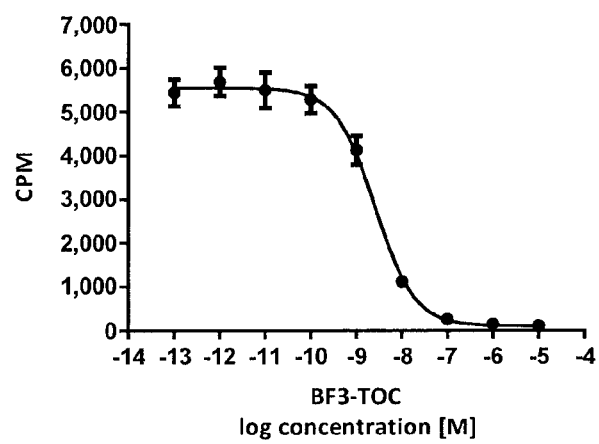
FIG. 11 depicts a representative competitive binding assay for $AMBF_3$-TOC using [$^{125}I$]-$Tyr^{11}$-somatostatin-14 as the displaced radioligand. The y-axis represents the amount of radioactivity bound to sstr2a receptors (CPM=counts per minute) and the x-axis represents the logarithmic molar concentration of $BF_3$-TOC. n=3.

The inhibition constant (Ki) of $AMBF_3$-TOC measured in sstr2a receptors with [$^{125}$I]-Tyr$^{11}$-somatostatin-14 as the displaced radioligand was 2.285±1.266 nM (n=3, mean±SD). A representative competition assay curve is shown in FIG. 11.

PET/CT Imaging

Figure 12:
FIG. 12 presents (A) a fused PET/CT coronal image showing high tumour and kidney uptake of $^{18}F$-$AMBF_3$-TOC, and (B) a maximum-intensity-projection image showing uptake of $^{18}F$-$AMBF_3$-TOC in tumour (t), kidneys (k), intestine (i) and bladder (b). Both color bars are calibrated in % ID/g.

The average tumour uptake based on the whole tumour region of interest was 3.15±0.80% ID/g and the uptake based on the hottest 2×2 voxel cluster was 7.40±0.28% ID/g (Mean±SD, n=2). The uptake in the left kidney, right kidney, heart contents and bone was 8.55±3.32% ID/g, 8.70±3.11% ID/g, 0.55±0.076% ID/g and 0.34±0.0028% ID/g, respectively. A representative PET/CT image is shown in FIG. 12.

Biodistribution

Figure 13:
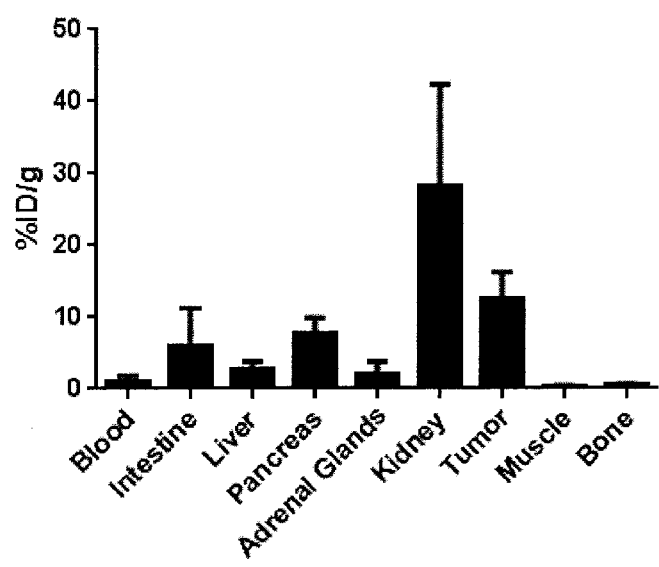
FIG. 13 shows tissue uptake of $^{18}F$-$AMBF_3$-TOC in % ID/g in certain organs of interest as determined by biodistribution 75 minutes post-injection. Values are displayed as mean+SD. n=4.

The ex vivo biodistribution data is listed in Table 3, and the values for certain tissues of interest are graphically displayed in FIG. 13. Tumour uptake was 12.57±3.66% ID/g. Uptake values in blood, muscle and bone were low compared to tumour: 1.15±0.66% ID/g, 0.26±0.13% ID/g and 0.56%±0.09% ID/g, respectively. There was some uptake in the pancreas (7.92±1.98% ID/g) as expected for an sstr2a positive tissue. The tumour-to-blood and tumour-to-muscle ratios were 10.93±0.64 and 48.35±0.58, respectively.

TABLE 3

Biodistribution of $^{18}$F-AMBF3-TOC (% ID/g) (n = 4)

| Tissues | Average | SD |
| --- | --- | --- |
| Blood | 1.15 | 0.66 |
| Fat | 0.17 | 0.12 |
| Uterus | 1.17 | 0.50 |
| Intestine | 6.21 | 5.06 |
| Stomach | 1.68 | 0.18 |
| Spleen | 1.35 | 0.29 |
| Liver | 2.88 | 0.90 |
| Pancreas | 7.92 | 1.98 |
| Adrenal Glands | 2.23 | 1.52 |
| Kidney | 28.48 | 13.89 |
| Lungs | 13.80 | 6.47 |
| Heart | 0.63 | 0.25 |
| Tumour | 12.57 | 3.66 |
| Muscle | 0.26 | 0.13 |
| Bone | 0.56 | 0.09 |
| Brain | 0.06 | 0.01 |
| Tail | 1.80 | 0.67 |

Example 7: Preparation of $AMBF_3$-JR11

Synthesis of azidoacetyl-JR11

Azidoacetyl-JR11 was synthesized via the $N^\alpha$-Fmoc solid-phase peptide synthesis strategy starting from D-Tyr-Rink Amide MBHA resin. The resin was treated with 20% piperidine in DMF to remove the $N^\alpha$-Fmoc protecting group. The following Fmoc-protected amino acids (3 equivalents) including Fmoc-Cys(Acm)-OH, Fmoc-Thr(tBu)-OH, Fmoc-Lys(Boc)-OH, Fmoc-D-Aph(Cbm)-OH, Fmoc-Aph(Hor)-OH, Fmoc-D-Cys(Acm)-OH, Fmoc-Cl-Phe-OH were subsequently coupled to the sequence in correct order. The coupling was carried out in NMP with standard in situ activating reagent HBTU/HOBT (3 equivalents) in the presence of DIEA (6 equivalents). Cyclization was performed by incubation of the resin with 2 equivalents of thallium(III) trifluoroacetate in DMF at room temperature for 90 min. Finally, azidoacetic acid (10 equivalents) was pre-activated with DIC (5 equivalents) in DCM for 10 min, filtered, and then coupled to the peptide sequence to provide the azide functional group at the N-terminus for click reaction.

The peptide was de-protected and simultaneously cleaved from the resin by the treatment of a cocktail of trifluoroacetic acid/water/triisopropylsilane (95:2.5:2.5). After filtration, the peptide was precipitated by the addition of cold diethyl ether to the TFA solution. The crude product was filtered, dried, and purified by HPLC (Luna C18 semi-prep column, 4.5 mL/min, 30-35% MeCN (0.1% TFA) in water (0.1% TFA), RT=10). Azidoacetyl-JR11 was obtained in 19% yield. ESI-MS: calculated for Azidoacetyl-JR11 $C_{60}H_{73}ClN_{18}O_{15}S_2$ 1384.5. found $[M+H]^+$ 1385.8.

Synthesis of $AMBF_3$-JR11

An Eppendorf tube (1.5 mL) was charged with a mixture of N-propargyl-N,N-dimethylammonio-methyltrifluoroborate (2.9 mg, 17.7 µmol), $CuSO_4$ (1.0 M, 5.0 µL), sodium ascorbate (1.0 M, 12.5 µL), 5% $NH_4OH$ ($MeCN/H_2O$=1:1, 50 µL) and azidoacetyl-JR11 (8.1 mg, 5.9 µmol). The mixture was warmed up to 45° C. for 2 h. Purification was performed by HPLC (Luna C18 semi-prep column) using conditions: 4.5 mL/min, 25-30% MeCN (0.1% TFA) in water (0.1% TFA), RT=13) to isolate to isolate 5.6 mg of $AMBF_3$-JR11 (compound 7, FIG. 8) (61%).

The disclosures of all patents, patent applications, publications and database entries referenced in this specification are hereby specifically incorporated by reference in their entirety to the same extent as if each such individual patent, patent application, publication and database entry were specifically and individually indicated to be incorporated by reference.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

The embodiments of the invention in which an exclusive property or privilege is claimed are defined as follows:

1. A fluorinated somatostatin derivative having general formula (I):

B⁻F₃—(CH₂)ₙ—N⁺R¹R²-L-X    (I)

wherein:

B is boron;

$R^1$ and $R^2$ are each independently H, $C_1$-$C_6$ alkyl, $C_3$-$C_6$ cycloalkyl, or $C_3$-$C_6$ aryl;

L is a linking group;

X is a somatostatin analogue conjugated via an N-terminal amino group to L, and n is 1 or 2, and wherein the somatostatin analogue is octreotide, octreotate, [Tyr³]octreotate (TATE), JR-11, JR-10, LM3, [Tyr³]octreotide (TOC) or [Nal³]octreotide (NOC).

2. The fluorinated somatostatin derivative according to claim 1, wherein n is 1.

3. The fluorinated somatostatin derivative according to claim 1, wherein $R^1$ and $R^2$ are each independently $C_1$-$C_6$ alkyl, or wherein the fluorinated somatostatin derivative has general formula (IV):

B⁻F₃—CH₂—N⁺(Me)₂-L-X    (IV), wherein L and X are as defined for formula (I).

4. The fluorinated somatostatin derivative according to claim 1, wherein:

L comprises a 1,2,3-triazole moiety

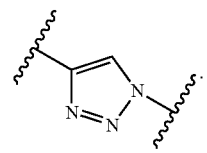 [SMILES: *c1cn(*)nn1]

5. The fluorinated somatostatin derivative according to claim 1, wherein:

the fluorinated somatostatin derivative has general formula (V)

wherein m and p are each independently 1 to 8, and wherein n and X are as defined for formula I; or the fluorinated somatostatin derivative has general formula (VI)

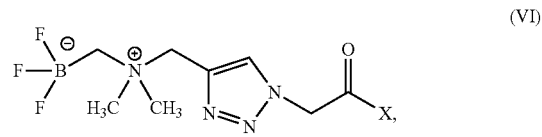

wherein X is as defined for formula I.

6. The fluorinated somatostatin derivative according to claim 1, wherein the somatostatin analogue is TATE, JR-11, LM3 or TOC.

7. The fluorinated somatostatin derivative according to claim 1, selected from: $AMBF_3$-TATE (compound 2), $AMBF_3$-JR11 (compound 7), $AMBF_3$-LM3 (compound 3) and $AMBF_3$-TOC (compound 6).

8. The fluorinated somatostatin derivative according to claim 1, wherein each F is $^{19}F$ or at least one F is $^{18}F$.

9. A method of preparing a $^{18}F$-labelled somatostatin derivative comprising contacting a fluorinated somatostatin derivative according to claim 1, wherein each F is $^{19}F$, with $^{18}F$-fluoride under conditions suitable for isotope exchange.

10. The method according to claim 9, wherein the $^{18}F$-fluoride is a no carrier added $^{18}F$-fluoride.

11. A method of imaging cells or tissues expressing somatostatin receptors, the method comprising:
   administering a fluorinated somatostatin derivative according to claim 1 to a subject, wherein at least one F is $^{18}F$; and
   imaging the subject for the presence of the fluorinated somatostatin derivative.

12. The method of claim 11, wherein the imaging is positron emission tomography (PET).

13. A method of imaging a cancer that expresses somatostatin receptors, the method comprising:
   administering a fluorinated somatostatin derivative according to claim 1 to a subject, wherein at least one F is $^{18}F$; and
   imaging the subject for the presence of the fluorinated somatostatin derivative;
   wherein the cancer is a neuroendocrine tumour, breast cancer, small cell lung cancer, lymphoma, meningioma, pituitary adenoma or pancreatic cancer.

14. A method of treating a disease or disorder, the method comprising administering the fluorinated somatostatin derivative of claim 8 to a subject, wherein the disease or disorder is a neuroendocrine tumour, breast cancer, small cell lung cancer, lymphoma, meningioma, pituitary adenoma or pancreatic cancer.

15. A kit for the preparation of a $^{18}F$-labelled imaging agent comprising the fluorinated somatostatin derivative according to claim 1, wherein each F is $^{19}F$, and optionally instructions for use.

16. The kit according to claim 15, wherein the kit comprises one or more containers and the somatostatin derivative is provided in the one or more containers in an effective amount to provide a single dose of the $^{18}F$-labelled imaging agent or multiple doses of the $^{18}F$-labelled imaging agent.

17. The fluorinated somatostatin derivative according to claim 1, wherein:
   L comprises formula (II)

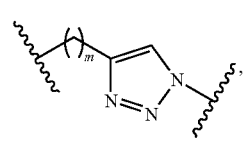

(II)

wherein m is 1 to 15.

18. The fluorinated somatostatin derivative according to claim 1, wherein:
   L is a linking group of formula (III)

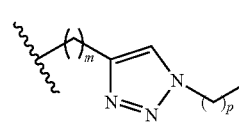

(III)

wherein m and p are each independently 1 to 8.

19. The method of claim 14, wherein each F in the somatostatin derivative is $^{19}F$.

* * * * *

SEQUENCE LISTING

```
<160> NUMBER OF SEQ ID NOS: 2

<210> SEQ ID NO 1
<211> LENGTH: 14
<212> TYPE: PRT
<213> ORGANISM: Homo sapiens
<220> FEATURE:
<221> NAME/KEY: DISULFID
<222> LOCATION: (3)..(14)
<223> OTHER INFORMATION: Somatostatin-14

<400> SEQUENCE: 1

Ala Gly Cys Lys Asn Phe Phe Trp Lys Thr Phe Thr Ser Cys
1               5                   10

<210> SEQ ID NO 2
<211> LENGTH: 28
<212> TYPE: PRT
<213> ORGANISM: Homo sapiens
<220> FEATURE:
<221> NAME/KEY: DISULFID
<222> LOCATION: (17)..(28)
<223> OTHER INFORMATION: Somatostatin-28

<400> SEQUENCE: 2

Ser Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25
```